United States Patent
Cohen et al.

(10) Patent No.: US 8,241,228 B1
(45) Date of Patent: Aug. 14, 2012

(54) MICRO-SCALE AND MESO-SCALE HYDRAULIC AND PNEUMATIC TOOLS, METHODS FOR USING, AND METHODS FOR MAKING

(75) Inventors: Adam L. Cohen, Los Angeles, CA (US); Chris R. Folk, Los Angeles, CA (US); Richard T. Chen, Woodland Hills, CA (US); Dennis R. Smalley, Newhall, CA (US)

(73) Assignee: Microfabrica Inc., Van Nuys, CA (US)

( * ) Notice: Subject to any disclaimer, the term of this patent is extended or adjusted under 35 U.S.C. 154(b) by 1065 days.

(21) Appl. No.: 12/139,445

(22) Filed: Jun. 13, 2008

Related U.S. Application Data

(63) Continuation-in-part of application No. 12/138,404, filed on Jun. 12, 2008, now abandoned, and a continuation-in-part of application No. 12/138,395, filed on Jun. 12, 2008, now abandoned, and a continuation-in-part of application No. 12/134,188, filed on Jun. 5, 2008, now abandoned, and a continuation-in-part of application No. 11/696,722, filed on Apr. 4, 2007, now abandoned, and a continuation-in-part of application No. 11/625,807, filed on Jan. 22, 2007, now abandoned, and a continuation-in-part of application No. 11/582,049, filed on Oct. 16, 2006, now Pat. No. 7,686,770, and a continuation-in-part of application No. 11/441,578, (Continued)

(51) Int. Cl.
*A61B 5/00* (2006.01)

(52) U.S. Cl. ............ 600/573; 417/415; 403/351
(58) Field of Classification Search ............ 600/573; 417/415; 402/251
See application file for complete search history.

(56) References Cited

U.S. PATENT DOCUMENTS 5,788,468 A * 8/1998 Dewa et al. .......... 417/415

(Continued)

*Primary Examiner* — Max Hindenburg
*Assistant Examiner* — Renee Danega
(74) *Attorney, Agent, or Firm* — Dennis R. Smalley

(57) ABSTRACT

Embodiments are directed to micro-scale or meso-scale hydraulically or pneumatically actuated devices, methods for forming such devices using multi-layer, multi-material electrochemical fabrication methods and particularly fabricating (i.e. building up) a plurality of components of devices that are moveable relative to one another in pre-assembled configurations wherein special features are designed into the devices (e.g. wide gaps in fabrication positions and narrowed gaps in working regions of component movement, mechanisms that inhibit the return of device components to fabrication positions after being moved into working regions, used of cylindrical interference and/or checkerboard bushings, etching holes in selected locations to allow removal of sacrificial material) to allow such fabrication to occur without violating intra-layer minimum feature size constraints while still obtaining effective gaps between components that are smaller than the minimum features size limits. Particular applications of such devices involve medical applications and in particular minimally invasive procedures where devices would be moved into a desired working area within a body of a patient via a lumen and then actuated while at the working location.

17 Claims, 24 Drawing Sheets

Related U.S. Application Data filed on May 26, 2006, now Pat. No. 7,674,361, and a continuation-in-part of application No. 10/949,744, filed on Sep. 24, 2004, now Pat. No. 7,498,714.

(60) Provisional application No. 60/968,863, filed on Aug. 29, 2007, provisional application No. 60/943,871, filed on Jun. 14, 2007, provisional application No. 60/951,711, filed on Jul. 24, 2007, provisional application No. 60/968,042, filed on Aug. 24, 2007, provisional application No. 61/018,283, filed on Dec. 31, 2007, provisional application No. 60/506,016, filed on Sep. 24, 2003, provisional application No. 60/942,200, filed on Jun. 5, 2007, provisional application No. 60/943,310, filed on Jun. 12, 2007, provisional application No. 60/949,850, filed on Jul. 14, 2007, provisional application No. 60/951,711, filed on Jul. 24, 2007, provisional application No. 60/945,570, filed on Jun. 21, 2007, provisional application No. 60/951,707, filed on Jul. 24, 2007, provisional application No. 60/968,043, filed on Aug. 24, 2007, provisional application No. 61/018,303, filed on Dec. 31, 2007, provisional application No. 60/943,309, filed on Jun. 12, 2007, provisional application No. 60/968,882, filed on Aug. 29, 2007, provisional application No. 60/943,318, filed on Jun. 12, 2007, provisional application No. 60/789,378, filed on Apr. 4, 2006, provisional application No. 60/726,794, filed on Oct. 14, 2005, provisional application No. 60/685,130, filed on May 26, 2005.

(56) References Cited

U.S. PATENT DOCUMENTS

| | | | |
|---|---|---|---|
| 7,029,249 B2 * | 4/2006 | Bougamont et al. | 417/511 |
| 7,960,935 B2 * | 6/2011 | Farritor et al. | 318/568.12 |
| 2003/0023189 A1 * | 1/2003 | Kuo | 600/584 |
| 2004/0006335 A1 * | 1/2004 | Garrison | 606/27 |

* cited by examiner

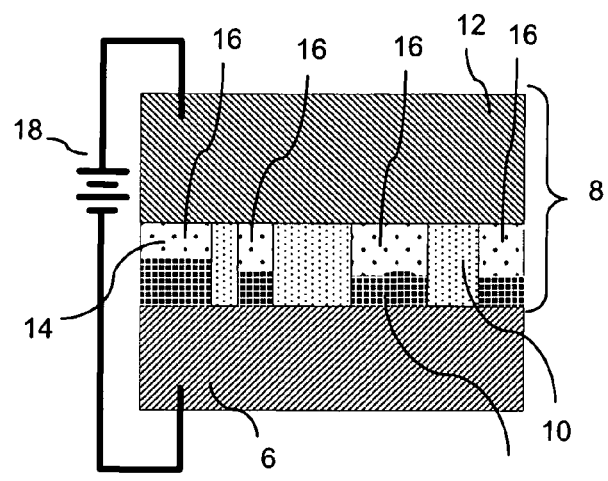
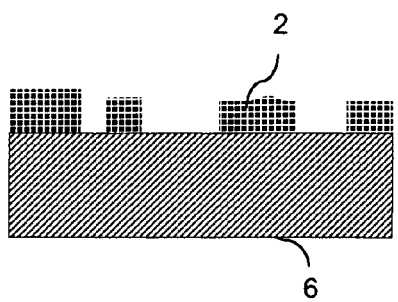
FIG. 2A
(PRIOR ART)
FIG. 2B
(PRIOR ART)
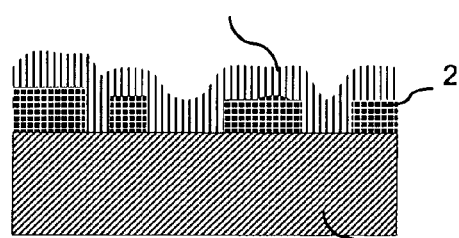
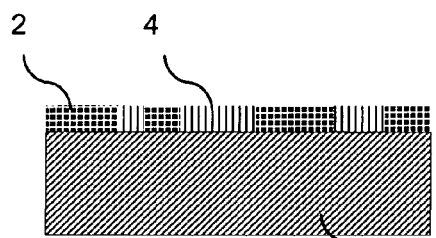
FIG. 2C
(PRIOR ART)
FIG. 2D
(PRIOR ART)
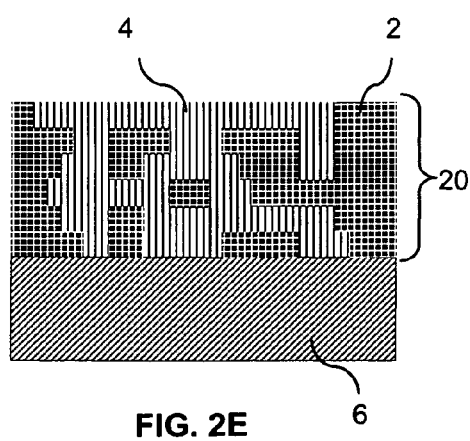
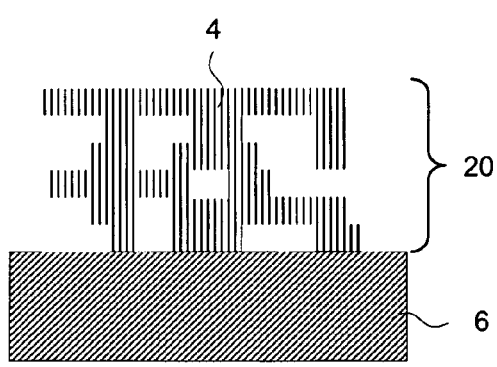
FIG. 2E
(PRIOR ART)
FIG. 2F
(PRIOR ART)

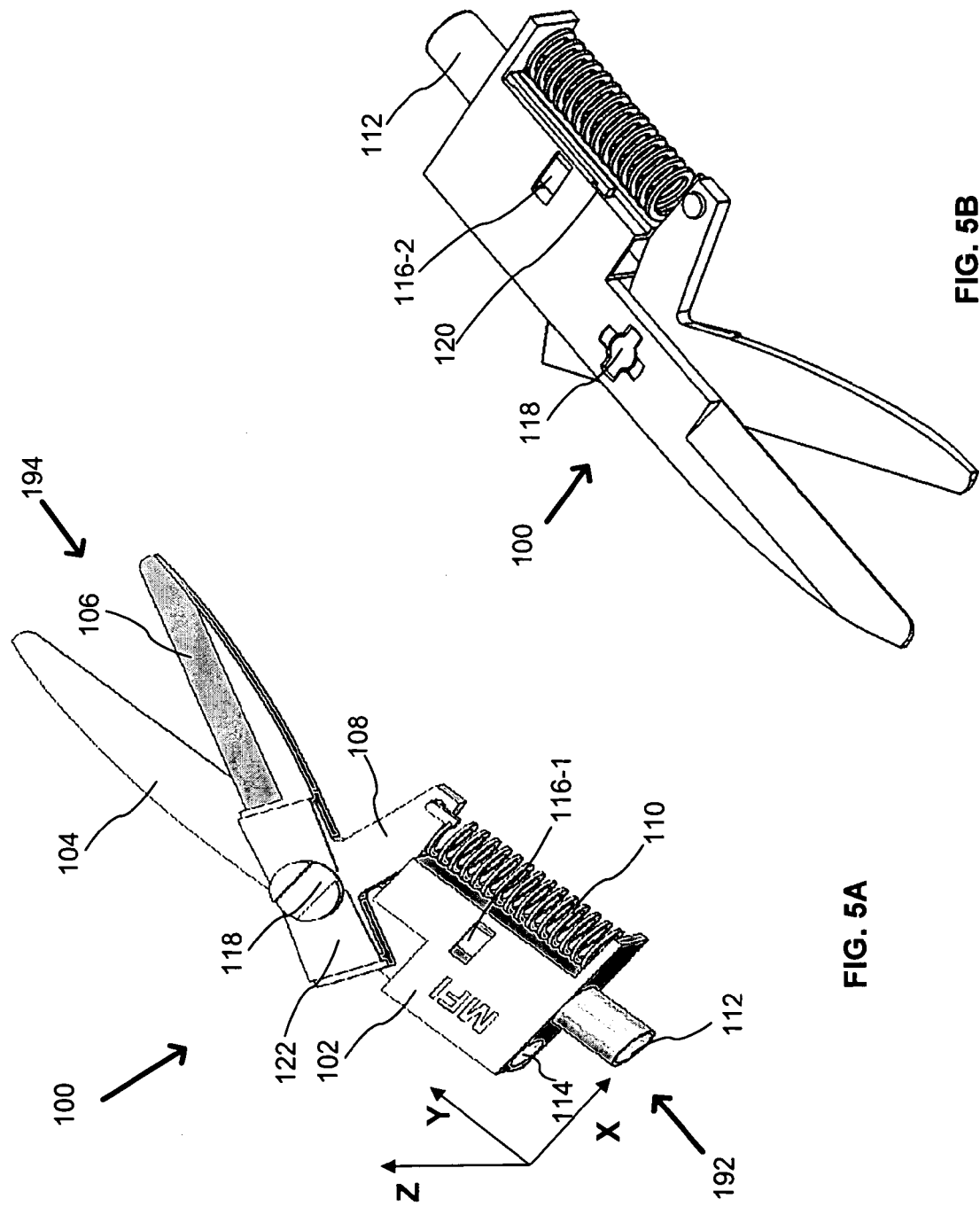

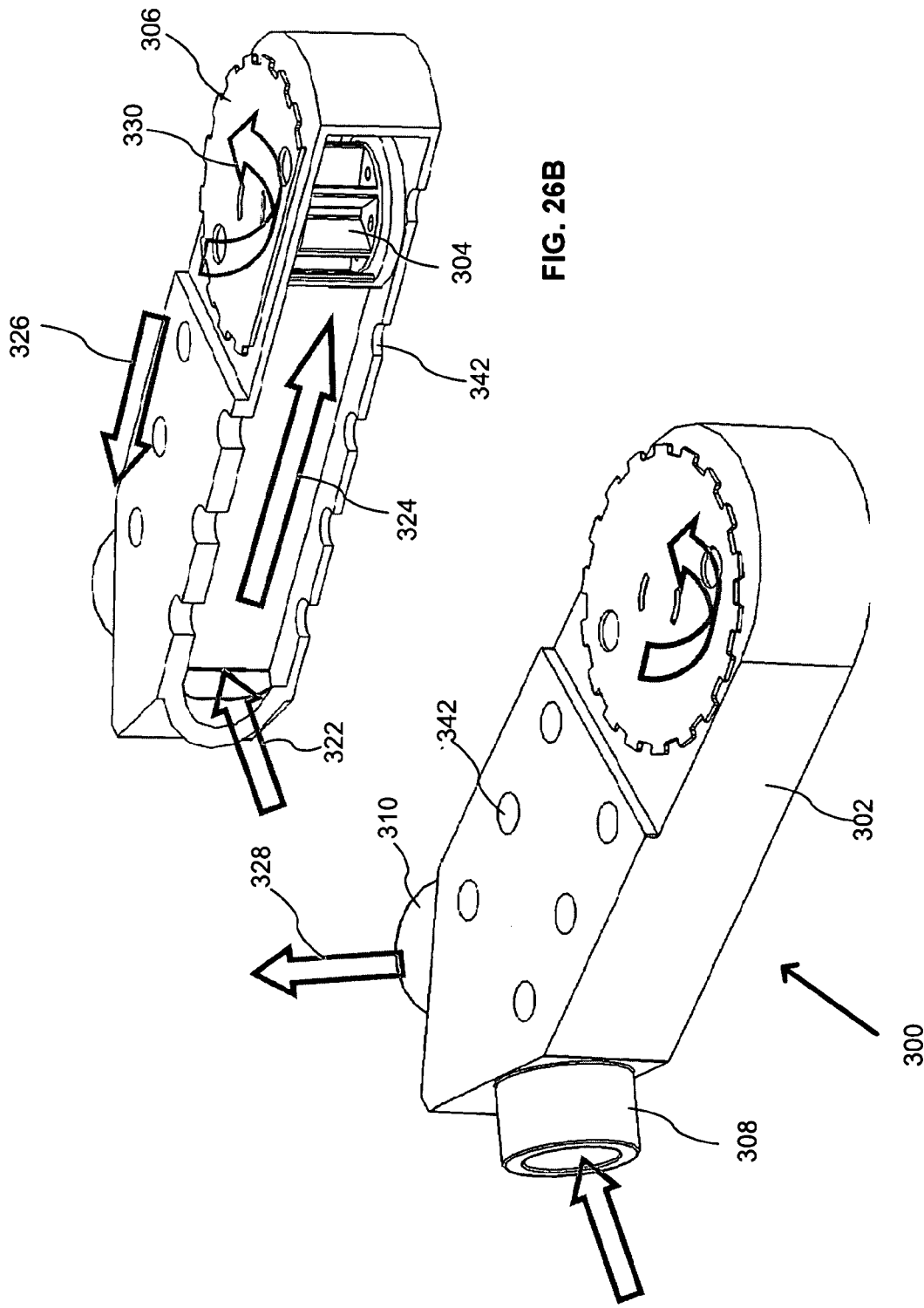

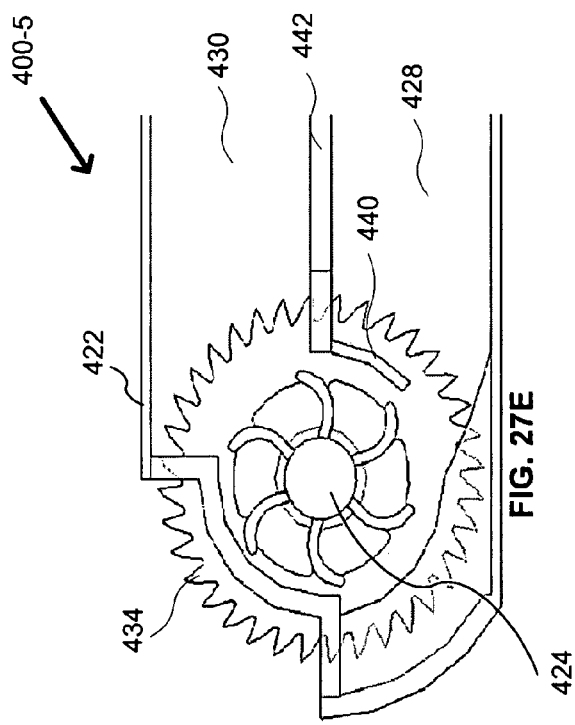
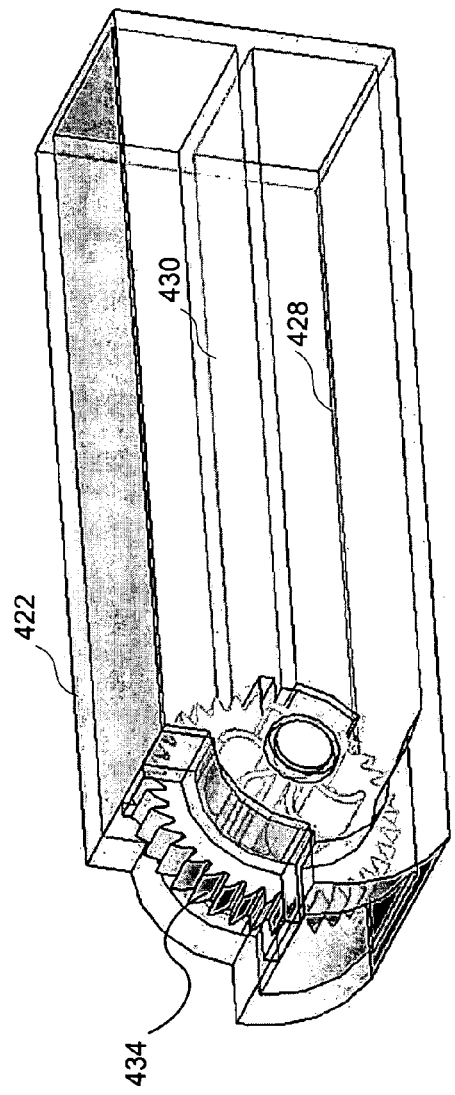
FIG. 27E
FIG. 27F

MICRO-SCALE AND MESO-SCALE HYDRAULIC AND PNEUMATIC TOOLS, METHODS FOR USING, AND METHODS FOR MAKING

RELATED APPLICATIONS

This application claims benefit of U.S. Patent Application Nos. 60/968,863, filed Aug. 29, 2007; and 60/943,871, filed Jun. 14, 2007; and 60/951,711 filed Jul. 24, 2007; and 60/968,042, filed Aug. 24, 2007; and 61/018,283, filed Dec. 31, 2007; and this application is a CIP of U.S. patent application Ser. Nos. 10/949,744, filed Sep. 24, 2004 now U.S. Pat. No. 7,498,714; and 12/134,188, filed Jun. 5, 2008 now abandoned; 12/138,404, filed Jun. 12, 2008 now abandoned; 12/138,395, filed Jun. 12, 2008 now abandoned and 11/441,578, filed May 26, 2006 now U.S. Pat. No. 7,674,361; the '744 application in turn claims benefit of 60/506,016, filed Sep. 24, 2003; the '188 application in turn claims benefit of U.S. Provisional Application Nos. 60/942,200; filed Jun. 5, 2007; 60/943,310, filed Jun. 12, 2007; 60/949,850, filed Jul. 14, 2007; 60/951,711, filed Jul. 24, 2007; 60/968,042, filed Aug. 24, 2007; and 61/018,283, filed Dec. 31, 2007; 60/945,570, filed Jun. 21, 2007; 60/951,707, filed Jul. 24, 2007; 60/968,043, filed Aug. 24, 2007; and 61/018,303, filed Dec. 31, 2007; and the '188 application is a CIP of U.S. patent application Ser. No. 11/625,807, filed Jan. 22, 2007 now abandoned; the '404 application in turn claims benefit of U.S. Provisional Application Nos. 60/943,309, filed Jun. 12, 2007; and 60/968,882, filed Aug. 29, 2007; the '395 application claims benefit of U.S. Patent Application No. 60/943,318, filed Jun. 12, 2007, and the '395 application is a continuation-in-part of U.S. patent application Ser. No. 11/696,722, filed Apr. 4, 2007 now abandoned which in turn claims benefit of U.S. Provisional Patent Application No. 60/789,378, filed Apr. 4, 2006, and is a continuation-in-part of U.S. patent application Ser. No. 11/582,049, filed Oct. 16, 2006 now U.S. Pat. No. 7,686,770 which in turn claims benefit of U.S. Provisional Patent Application No. 60/726,794, filed Oct. 14, 2005; and the '578 application claims benefit of 60/685,130, filed May 26, 2005. Each of these applications is incorporated herein by reference as if set forth in full herein.

FIELD OF THE INVENTION

The present invention relates generally to the field of micro- or meso-scale hydraulic or pneumatic devices and to the use of multi-layer, multi-material electrochemical fabrication methods for producing such devices, particular embodiments relate to hydraulic and/or pneumatic medical devices and particularly to medical tools that may be useful in surgical procedures and in particular for minimally invasive procedures.

BACKGROUND OF THE INVENTION

Electrochemical Fabrication:

An electrochemical fabrication technique for forming three-dimensional structures from a plurality of adhered layers is being commercially pursued by Microfabrica® Inc. (formerly MEMGen Corporation) of Van Nuys, Calif. under the name EFAB®.

Various electrochemical fabrication techniques were described in U.S. Pat. No. 6,027,630, issued on Feb. 22, 2000 to Adam Cohen. Some embodiments of this electrochemical fabrication technique allows the selective deposition of a material using a mask that includes a patterned conformable material on a support structure that is independent of the substrate onto which plating will occur. When desiring to perform an electrodeposition using the mask, the conformable portion of the mask is brought into contact with a substrate, but not adhered or bonded to the substrate, while in the presence of a plating solution such that the contact of the conformable portion of the mask to the substrate inhibits deposition at selected locations. For convenience, these masks might be generically called conformable contact masks; the masking technique may be generically called a conformable contact mask plating process. More specifically, in the terminology of Microfabrica Inc. such masks have come to be known as INSTANT MASKS™ and the process known as INSTANT MASKING™ or INSTANT MASK™ plating. Selective depositions using conformable contact mask plating may be used to form single selective deposits of material or may be used in a process to form multi-layer structures. The teachings of the '630 patent are hereby incorporated herein by reference as if set forth in full herein. Since the filing of the patent application that led to the above noted patent, various papers about conformable contact mask plating (i.e. INSTANT MASKING) and electrochemical fabrication have been published:

(1) A. Cohen, G. Zhang, F. Tseng, F. Mansfeld, U. Frodis and P. Will, "EFAB: Batch production of functional, fully-dense metal parts with micro-scale features", Proc. 9th Solid Freeform Fabrication, The University of Texas at Austin, p 161, August 1998.

(2) A. Cohen, G. Zhang, F. Tseng, F. Mansfeld, U. Frodis and P. Will, "EFAB: Rapid, Low-Cost Desktop Micromachining of High Aspect Ratio True 3-D MEMS", Proc. 12th IEEE Micro Electro Mechanical Systems Workshop, IEEE, p 244, January 1999.

(3) A. Cohen, "3-D Micromachining by Electrochemical Fabrication", Micromachine Devices, March 1999.

(4) G. Zhang, A. Cohen, U. Frodis, F. Tseng, F. Mansfeld, and P. Will, "EFAB: Rapid Desktop Manufacturing of True 3-D Microstructures", Proc. 2nd International Conference on Integrated MicroNanotechnology for Space Applications, The Aerospace Co., April 1999.

(5) F. Tseng, U. Frodis, G. Zhang, A. Cohen, F. Mansfeld, and P. Will, "EFAB: High Aspect Ratio, Arbitrary 3-D Metal Microstructures using a Low-Cost Automated Batch Process", 3rd International Workshop on High Aspect Ratio MicroStructure Technology (HARMST'99), June 1999.

(6) A. Cohen, U. Frodis, F. Tseng, G. Zhang, F. Mansfeld, and P. Will, "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, September 1999.

(7) F. Tseng, G. Zhang, U. Frodis, A. Cohen, F. Mansfeld, and P. Will, "EFAB: High Aspect Ratio, Arbitrary 3-D Metal Microstructures using a Low-Cost Automated Batch Process", MEMS Symposium, ASME 1999 International Mechanical Engineering Congress and Exposition, November, 1999.

(8) A. Cohen, "Electrochemical Fabrication (EFAB™)", Chapter 19 of The MEMS Handbook, edited by Mohamed Gad-El-Hak, CRC Press, 2002.

(9) Microfabrication—Rapid Prototyping's Killer Application", pages 1-5 of the Rapid Prototyping Report, CAD/CAM Publishing, Inc., June 1999.

The disclosures of these nine publications are hereby incorporated herein by reference as if set forth in full herein.

An electrochemical deposition for forming multilayer structures may be carried out in a number of different ways as set forth in the above patent and publications. In one form, this process involves the execution of three separate operations during the formation of each layer of the structure that is to be formed:

1. Selectively depositing at least one material by electrodeposition upon one or more desired regions of a substrate. Typically this material is either a structural material or a sacrificial material.
2. Then, blanket depositing at least one additional material by electrodeposition so that the additional deposit covers both the regions that were previously selectively deposited onto, and the regions of the substrate that did not receive any previously applied selective depositions. Typically this material is the other of a structural material or a sacrificial material.
3. Finally, planarizing the materials deposited during the first and second operations to produce a smoothed surface of a first layer of desired thickness having at least one region containing the at least one material and at least one region containing at least the one additional material.

After formation of the first layer, one or more additional layers may be formed adjacent to an immediately preceding layer and adhered to the smoothed surface of that preceding layer. These additional layers are formed by repeating the first through third operations one or more times wherein the formation of each subsequent layer treats the previously formed layers and the initial substrate as a new and thickening substrate.

Once the formation of all layers has been completed, at least a portion of at least one of the materials deposited is generally removed by an etching process to expose or release the three-dimensional structure that was intended to be formed. The removed material is a sacrificial material while the material that forms part of the desired structure is a structural material.

The preferred method of performing the selective electrodeposition involved in the first operation is by conformable contact mask plating. In this type of plating, one or more conformable contact (CC) masks are first formed. The CC masks include a support structure onto which a patterned conformable dielectric material is adhered or formed. The conformable material for each mask is shaped in accordance with a particular cross-section of material to be plated (the pattern of conformable material is complementary to the pattern of material to be deposited). At least one CC mask is used for each unique cross-sectional pattern that is to be plated.

The support for a CC mask is typically a plate-like structure formed of a metal that is to be selectively electroplated and from which material to be plated will be dissolved. In this typical approach, the support will act as an anode in an electroplating process. In an alternative approach, the support may instead be a porous or otherwise perforated material through which deposition material will pass during an electroplating operation on its way from a distal anode to a deposition surface. In either approach, it is possible for multiple CC masks to share a common support, i.e. the patterns of conformable dielectric material for plating multiple layers of material may be located in different areas of a single support structure. When a single support structure contains multiple plating patterns, the entire structure is referred to as the CC mask while the individual plating masks may be referred to as "submasks". In the present application such a distinction will be made only when relevant to a specific point being made.

In preparation for performing the selective deposition of the first operation, the conformable portion of the CC mask is placed in registration with and pressed against a selected portion of (1) the substrate, (2) a previously formed layer, or (3) a previously deposited portion of a layer on which deposition is to occur. The pressing together of the CC mask and relevant substrate occur in such a way that all openings, in the conformable portions of the CC mask contain plating solution. The conformable material of the CC mask that contacts the substrate acts as a barrier to electrodeposition while the openings in the CC mask that are filled with electroplating solution act as pathways for transferring material from an anode (e.g. the CC mask support) to the non-contacted portions of the substrate (which act as a cathode during the plating operation) when an appropriate potential and/or current are supplied.

An example of a CC mask and CC mask plating are shown in FIGS. 1A-1C. FIG. 1A shows a side view of a CC mask 8 consisting of a conformable or deformable (e.g. elastomeric) insulator 10 patterned on an anode 12. The anode has two functions. One is as a supporting material for the patterned insulator 10 to maintain its integrity and alignment since the pattern may be topologically complex (e.g., involving isolated "islands" of insulator material). The other function is as an anode for the electroplating operation. FIG. 1A also depicts a substrate 6, separated from mask 8, onto which material will be deposited during the process of forming a layer. CC mask plating selectively deposits material 22 onto substrate 6 by simply pressing the insulator against the substrate then electrodepositing material through apertures 26a and 26b in the insulator as shown in FIG. 1B. After deposition, the CC mask is separated, preferably non-destructively, from the substrate 6 as shown in FIG. 1C.

The CC mask plating process is distinct from a "through-mask" plating process in that in a through-mask plating process the separation of the masking material from the substrate would occur destructively. Furthermore in a through mask plating process, opening in the masking material are typically formed while the masking material is in contact with and adhered to the substrate. As with through-mask plating, CC mask plating deposits material selectively and simultaneously over the entire layer. The plated region may consist of one or more isolated plating regions where these isolated plating regions may belong to a single structure that is being formed or may belong to multiple structures that are being formed simultaneously. In CC mask plating as individual masks are not intentionally destroyed in the removal process, they may be usable in multiple plating operations.

Another example of a CC mask and CC mask plating is shown in FIGS. 1D-1G. FIG. 1D shows an anode 12' separated from a mask 8' that includes a patterned conformable material 10' and a support structure 20. FIG. 1D also depicts substrate 6 separated from the mask 8'. FIG. 1E illustrates the mask 8' being brought into contact with the substrate 6. FIG. 1F illustrates the deposit 22' that results from conducting a current from the anode 12' to the substrate 6. FIG. 1G illustrates the deposit 22' on substrate 6 after separation from mask 8'. In this example, an appropriate electrolyte is located between the substrate 6 and the anode 12' and a current of ions coming from one or both of the solution and the anode are conducted through the opening in the mask to the substrate where material is deposited. This type of mask may be referred to as an anodeless INSTANT MASK™ (AIM) or as an anodeless conformable contact (ACC) mask.

Unlike through-mask plating, CC mask plating allows CC masks to be formed completely separate from the substrate on which plating is to occur (e.g. separate from a three-dimensional (3D) structure that is being formed). CC masks may be formed in a variety of ways, for example, using a photolithographic process. All masks can be generated simultaneously, e.g. prior to structure fabrication rather than during it. This separation makes possible a simple, low-cost, automated, self-contained, and internally-clean "desktop factory" that can be installed almost anywhere to fabricate 3D structures, leaving any required clean room processes, such as photolithography to be performed by service bureaus or the like.

An example of the electrochemical fabrication process discussed above is illustrated in FIGS. 2A-2F. These figures show that the process involves deposition of a first material 2 which is a sacrificial material and a second material 4 which is a structural material. The CC mask 8, in this example, includes a patterned conformable material (e.g. an elastomeric dielectric material) 10 and a support 12 which is made from deposition material 2. The conformal portion of the CC mask is pressed against substrate 6 with a plating solution 14 located within the openings 16 in the conformable material 10. An electric current, from power supply 18, is then passed through the plating solution 14 via (a) support 12 which doubles as an anode and (b) substrate 6 which doubles as a cathode. FIG. 2A illustrates that the passing of current causes material 2 within the plating solution and material 2 from the anode 12 to be selectively transferred to and plated on the substrate 6. After electroplating the first deposition material 2 onto the substrate 6 using CC mask 8, the CC mask 8 is removed as shown in FIG. 2B. FIG. 2C depicts the second deposition material 4 as having been blanket-deposited (i.e. non-selectively deposited) over the previously deposited first deposition material 2 as well as over the other portions of the substrate 6. The blanket deposition occurs by electroplating from an anode (not shown), composed of the second material, through an appropriate plating solution (not shown), and to the cathode/substrate 6. The entire two-material layer is then planarized to achieve precise thickness and flatness as shown in FIG. 2D. After repetition of this process for all layers, the multi-layer structure 20 formed of the second material 4 (i.e. structural material) is embedded in first material 2 (i.e. sacrificial material) as shown in FIG. 2E. The embedded structure is etched to yield the desired device, i.e. structure 20, as shown in FIG. 2F.

Various components of an exemplary manual electrochemical fabrication system 32 are shown in FIGS. 3A-3C. The system 32 consists of several subsystems 34, 36, 38, and 40. The substrate holding subsystem 34 is depicted in the upper portions of each of FIGS. 3A-3C and includes several components: (1) a carrier 48, (2) a metal substrate 6 onto which the layers are deposited, and (3) a linear slide 42 capable of moving the substrate 6 up and down relative to the carrier 48 in response to drive force from actuator 44. Subsystem 34 also includes an indicator 46 for measuring differences in vertical position of the substrate which may be used in setting or determining layer thicknesses and/or deposition thicknesses. The subsystem 34 further includes feet 68 for carrier 48 which can be precisely mounted on subsystem 36.

The CC mask subsystem 36 shown in the lower portion of FIG. 3A includes several components: (1) a CC mask 8 that is actually made up of a number of CC masks (i.e. submasks) that share a common support/anode 12, (2) precision X-stage 54, (3) precision Y-stage 56, (4) frame 72 on which the feet 68 of subsystem 34 can mount, and (5) a tank 58 for containing the electrolyte 16. Subsystems 34 and 36 also include appropriate electrical connections (not shown) for connecting to an appropriate power source (not shown) for driving the CC masking process.

The blanket deposition subsystem 38 is shown in the lower portion of FIG. 3B and includes several components: (1) an anode 62, (2) an electrolyte tank 64 for holding plating solution 66, and (3) frame 74 on which feet 68 of subsystem 34 may sit. Subsystem 38 also includes appropriate electrical connections (not shown) for connecting the anode to an appropriate power supply (not shown) for driving the blanket deposition process.

The planarization subsystem 40 is shown in the lower portion of FIG. 3C and includes a lapping plate 52 and associated motion and control systems (not shown) for planarizing the depositions.

In addition to teaching the use of CC masks for electrodeposition purposes, the '630 patent also teaches that the CC masks may be placed against a substrate with the polarity of the voltage reversed and material may thereby be selectively removed from the substrate. It indicates that such removal processes can be used to selectively etch, engrave, and polish a substrate, e.g., a plaque.

The '630 patent further indicates that the electroplating methods and articles disclosed therein allow fabrication of devices from thin layers of materials such as, e.g., metals, polymers, ceramics, and semiconductor materials. It further indicates that although the electroplating embodiments described therein have been described with respect to the use of two metals, a variety of materials, e.g., polymers, ceramics and semiconductor materials, and any number of metals can be deposited either by the electroplating methods therein, or in separate processes that occur throughout the electroplating method. It indicates that a thin plating base can be deposited, e.g., by sputtering, over a deposit that is insufficiently conductive (e.g., an insulating layer) so as to enable subsequent electroplating. It also indicates that multiple support materials (i.e. sacrificial materials) can be included in the electroplated element allowing selective removal of the support materials.

The '630 patent additionally teaches that the electroplating methods disclosed therein can be used to manufacture elements having complex microstructure and close tolerances between parts. An example is given with the aid of FIGS. 14A-14E of that patent. In the example, elements having parts that fit with close tolerances, e.g., having gaps between about 1-5 um, including electroplating the parts of the device in an unassembled, preferably pre-aligned, state and once fabricated. In such embodiments, the individual parts can be moved into operational relation with each other or they can simply fall together. Once together the separate parts may be retained by clips or the like.

Another method for forming microstructures from electroplated metals (i.e. using electrochemical fabrication techniques) is taught in U.S. Pat. No. 5,190,637 to Henry Guckel, entitled "Formation of Microstructures by Multiple Level Deep X-ray Lithography with Sacrificial Metal layers". This patent teaches the formation of metal structure utilizing through mask exposures. A first layer of a primary metal is electroplated onto an exposed plating base to fill a void in a photoresist (the photoresist forming a through mask having a desired pattern of openings), the photoresist is then removed and a secondary metal is electroplated over the first layer and over the plating base. The exposed surface of the secondary metal is then machined down to a height which exposes the first metal to produce a flat uniform surface extending across both the primary and secondary metals. Formation of a second layer may then begin by applying a photoresist over the first layer and patterning it (i.e. to form a second through mask) and then repeating the process that was used to produce the first layer to produce a second layer of desired configuration. The process is repeated until the entire structure is formed and the secondary metal is removed by etching. The photoresist is formed over the plating base or previous layer by casting and patterning of the photoresist (i.e. voids formed in the photoresist) are formed by exposure of the photoresist through a patterned mask via X-rays or UV radiation and development of the exposed or unexposed areas.

The '637 patent teaches the locating of a plating base onto a substrate in preparation for electroplating materials onto the substrate. The plating base is indicated as typically involving the use of a sputtered film of an adhesive metal, such as chromium or titanium, and then a sputtered film of the metal that is to be plated. It is also taught that the plating base may be applied over an initial layer of sacrificial material (i.e. a layer or coating of a single material) on the substrate so that the structure and substrate may be detached if desired. In such cases after formation of the structure the sacrificial material forming part of each layer of the structure may be removed along the initial sacrificial layer to free the structure. Substrate materials mentioned in the '637 patent include silicon, glass, metals, and silicon with protected semiconductor devices. A specific example of a plating base includes about 150 angstroms of titanium and about 300 angstroms of nickel, both of which are sputtered at a temperature of 160° C. In another example it is indicated that the plating base may consist of 150 angstroms of titanium and 150 angstroms of nickel where both are applied by sputtering.

Electrochemical Fabrication provides the ability to form prototypes and commercial quantities of miniature objects, parts, structures, devices, and the like at reasonable costs and in reasonable times. In fact, Electrochemical Fabrication is an enabler for the formation of many structures that were hitherto impossible to produce. Electrochemical Fabrication opens the spectrum for new designs and products in many industrial fields. Even though Electrochemical Fabrication offers this new capability and it is understood that Electrochemical Fabrication techniques can be combined with designs and structures known within various fields to produce new structures, certain uses for Electrochemical Fabrication provide designs, structures, capabilities and/or features not known or obvious in view of the state of the art.

A need exists in various fields for miniature devices having improved characteristics, reduced fabrication times, reduced fabrication costs, simplified fabrication processes, greater versatility in device design, improved selection of materials, improved material properties, more cost effective and less risky production of such devices, and/or more independence between geometric configuration and the selected fabrication process.

SUMMARY OF THE INVENTION

It is an object of some embodiments of the invention to provide improved micro-scale or meso-scale devices and in particular embodiments improved medical devices.

It is an object of some embodiments of the invention to provide improved methods for fabricating micro-scale or meso-scale devices.

It is an object of some embodiments of the invention to provide micro-scale or meso scale tools that have effective clearances, between structures that rotate or translate relative to other structures, that are substantially smaller than a minimum feature size. In some embodiments such effective clearances are achieved using (1) fabrication regions (e.g. with larger gaps) that are offset from working regions (with smaller gaps) and where the access to fabrication regions may be locked away from the working regions, (2) the moving parts are separated by interference bushings, (3) the moving parts are fabricated with offset protrusions along a build axis (e.g. Z or vertical axis) and/or along an axis of movement (e.g. an X-axis, a Y-axis, a Z-axis, or a combination thereof for a translating structure, or a radial and/or tangential axis for rotating structures); (4) tabs or protrusions that provide a clearance with the majority of the spacing between the relative moving structures being larger to allow more effective removal of sacrificial material; or (5) the moving structures brought into their desired positions after fabrication in an automatic or manual assembly process.

It is an object of some embodiments of the invention to provide devices (e.g. medical devices) or device components including multiple moving structures that are fabricated via the deposition of material while in an assembled state.

It is an object of some embodiments of the invention to provide meso-scale or micro-scale hydraulically and/or pneumatically actuated devices (e.g. medical devices) with improved characteristics, improved features, improved functionality, reduced fabrication cost, reduced assembly cost, and/or reduced fabrication time.

It is an object of some embodiments of the invention to provide meso-scale or micro-scale devices (e.g. medical devices) having pivots that lock the movable elements together while biasing the elements against each other and in some embodiments while the structures are fabricated simultaneously while located, primarily or even substantially, in their desired relative positions.

Other objects and advantages of various embodiments of the invention will be apparent to those of skill in the art upon review of the teachings herein. The various embodiments of the invention, set forth explicitly herein or otherwise ascertained from the teachings herein, may address one or more of the above objects alone or in combination, or alternatively may address some other object ascertained from the teachings herein. It is not necessarily intended that all objects be addressed by any single aspect of the invention even though that may be the case with regard to some aspects.

A first aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; wherein the device body and actuation mechanism include a fabrication position relative to each other that provides a spacing between a first portion of the actuation mechanism relative to a first portion of the device body that is at least as large as a minimum feature size; wherein the device body and actuation mechanism include a working range, which is displaced from the fabrication positions, in which the first portion of the actuation mechanism moves relative to the device body during normal operation of the device.

Numerous variations of the first aspect of the invention are possible, and include, for example, one or more of the following: (1) a tool element functionally connected to the actuation mechanism for interacting with material external to the device, wherein the tool element may be one or more of (i) a saw blade, (ii) a grinder, (iii) a hold and release mechanism, (iv) a clamp, (v) an expander, (vi) scissors, (vii) a reflector, (viii) a suction device, (ix) an irrigator, or (x) a transducer; (2) the tool is used in performance of a minimally invasive procedure located at a position that is reached after traversing a tortuous path (e.g. a neurosurgical procedure), (3) the tool element includes multiple components, one or more of which is functionally connected to the device body; (4) the first portion of the actuation mechanism is inhibited by one or more mechanical components from returning to the fabrication position during normal operation of the device; (5) the actuation mechanism includes a piston head and the passage is located within a piston cylinder, wherein the piston cylinder may be curved; (6) the actuation mechanism includes an impeller that can rotate relative to the device body; (7) relative movement between two elements of the device occurs at an interference bushing; (8) relative movement between two elements of the device occurs at a linear checkerboard bushing; (9) relative movement between two elements of the device occur at a cylindrical checkerboard bushing; (10) a fluid outlet that is different from the fluid inlet; (11) the device is a hydraulic device; (12) the device is a medical device for insertion into a body of a patient during a minimally invasive procedure wherein the device provides or aids in the providing a diagnostic evaluation of, therapeutic treatment on, or preventive treatment on the body of a patient; (13) the device is a pneumatic device; (14) the device is formed at least in part via a multi-layer, multi-material deposition process wherein each layer includes at least one sacrificial material and at least one structural material and wherein each layer undergoes a planarization process and wherein the sacrificial material is removed from a plurality of layers after formation of the plurality of layers.

A second aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; wherein a pair of surfaces around which a first element and second element of the device move past one another during operation and are separated by more than a minimum feature size on individual layers from which the device was formed but which provide an effective gap between the pair of surfaces, when taken as whole, which is substantially less than the minimum feature size, and wherein a fabrication position of the surfaces relative to one another is within a working range of the positions taken by the surfaces when the mechanism operates.

Numerous variations of the second aspect of the invention are possible, and may include, for example, the first element including at least a portion of the actuation mechanism while the second element includes a portion of the body of the device.

A third aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; wherein a pair of surfaces around which a first element and second element of the device move past one another during operation are separated by more than a minimum feature size on individual layers from which the device was formed; wherein the first and second elements are shifted relative to one another in a direction parallel to a stacking direction of the layers such that actual gaps between selected layers of the first element and selected layers of the second element are smaller than the minimum feature size; and wherein the relative shifting of the first and second elements is maintained by compliant element and a retention element.

A fourth aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; wherein the actuation mechanism includes a piston head having a curved shaft and the passage is defined by a curved piston cylinder.

A fifth aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; wherein the actuation mechanism includes a piston having a periphery punctuated by at least one of sealing tabs or full rings.

A sixth aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; and (c) a pair of scissor blades that move relative to one another via the movement of the actuation mechanism.

A variation of the sixth aspect of the invention may include the scissor blades being biased toward one another by a compliant element and they may be held in that position by a retention element.

A seventh aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; and (c) a pair of arms that provide a forceps functionality via the movement of the actuation mechanism.

A variation of the seventh aspect of the invention may include pivotable pads connected to the distal ends of each of the arms.

An eighth aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; and (c) a saw blade that rotates via the movement of the actuation mechanism.

A ninth aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; and (c) a flexure for returning the actuation mechanism to a desired position relative to the body of the device after removal of a force that caused initial movement of the actuation mechanism.

A tenth aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; and (c) a piston which acts upon fluid which activates sensory portion of the device or a separate actuation mechanism of the device.

A eleventh aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; wherein the device is configured for insertion into a body of a patient during a minimally invasive medical procedure via a guide element that feeds the device down a lumen and provides a flow path for fluid to the inlet of the device.

A twelfth aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; and (c) a compliant mechanism for at least partially closing gaps between at least two components, from which the device is formed, when transitioning from a loading position to a working range of the device.

A thirteenth aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; and (c) one or more ball bearings loaded into one or more openings in one or more components and which optionally may become trapped within desired locations in the component(s) when components of the device are maintained within a working range of the device.

A fourteenth aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; wherein at least two components, from which the device is formed move past one another along an interference bushing.

A fifteenth aspect of the invention provides a millimeter scale or microscale hydraulic or pneumatically actuated device, including: (a) a device body including an inlet for receiving a fluid flow and a passage for directing the fluid flow along a desired path through the body; (b) an actuation mechanism functionally connected to the fluid flow path which undergoes a desired mechanical movement in response to fluid flow in the passage; wherein the actuation mechanism includes a piston having a ring that is compressed when slid along a tapered surface into a working range.

Variations of each of the second through fifteenth aspects of the invention are possible and may include, for example, one or more of the following:(1) the first portion of the actuation mechanism is inhibited by one or more mechanical components from returning to the fabrication position during normal operation of the device; (2) relative movement between two elements of the device occurs at an interference bushing; (3) relative movement between two elements of the device occurs at a linear checkerboard bushing; (4) relative movement between two elements of the device occur at a cylindrical checkerboard bushing; (5) a fluid outlet that is different from the fluid inlet; (6) the device is a hydraulic device; (7) the device is a medical device for insertion into a body of a patient during a minimally invasive procedure wherein the device provides or aids in the providing a diagnostic evaluation of, therapeutic treatment on, or preventive treatment on the body of a patient; (8) the device is a pneumatic device; and/or (9) the device is formed at least in part via a multi-layer, multi-material deposition process wherein each layer includes at least one sacrificial material and at least one structural material and wherein each layer undergoes a planarization process and wherein the sacrificial material is removed from a plurality of layers after formation of the plurality of layers.

A sixteenth aspect of the invention provides a minimally invasive surgical procedure for providing a diagnostic or therapeutic treatment to a body of a patient, including: (a) inserting a lumen, having a distal end and a proximal end into the body of a patient such that the proximal end remains outside the body of the patient while the distal end is located in proximity to a desired location; (b) inserting a device into the lumen to provide the diagnostic or therapeutic treatment to a desired site within the body of the patient, wherein the device includes: (i) a device body including an inlet for receiving a fluid flow and a passage for directing the fluid flow along a desired path through the body; (ii) an actuation mechanism functionally connected to the fluid flow path which undergoes a desired mechanical movement in response to fluid flow in the passage; and (c) while at the desired site, operating the device to provide or aid in the provision of the diagnostic or therapeutic treatment.

Variations of the sixteenth aspect of the invention are possible and may include, for example, one or more of the following:(1) the first portion of the actuation mechanism is inhibited by one or more mechanical components from returning to the fabrication position during normal operation of the device; (2) relative movement between two elements of the device occurs at an interference bushing; (3) relative movement between two elements of the device occurs at a linear checkerboard bushing; (4) relative movement between two elements of the device occur at a cylindrical checkerboard bushing; (5) a fluid outlet that is different from the fluid inlet; (6) the device is a hydraulic device; (7) the device is a pneumatic device; and/or (8) the device is formed at least in part via a multi-layer, multi-material deposition process wherein each layer includes at least one sacrificial material and at least one structural material and wherein each layer undergoes a planarization process and wherein the sacrificial material is removed from a plurality of layers after formation of the plurality of layers.

Further variations of the sixteenth aspect of the invention are possible and may include the desired location being located at the end of a tortuous feed path and/or the procedure benefiting from haptic force or pressure feedback (e.g. robotic procedures).

A seventeenth aspect of the invention provides a method for fabricating a hydraulic or pneumatic microscale device, including: (a) forming a plurality of adhered layers of material, wherein the forming of each layer of material includes, (i) deposition of at least a first material; (ii) deposition of at least a second material; and (iii) planarization of the first and second materials to a common level; (b) removing of at least a portion of the first or second material from a plurality of layers after formation of the plurality of layers; wherein the device includes: (i) a device body including an inlet for receiving a fluid flow and a passage for directing the fluid flow along a desired path through the body; (ii) an actuation mechanism functionally connected to the fluid flow path which undergoes a desired mechanical movement in response to fluid flow in the passage; wherein the device includes multiple components, at least one of which can move relative to the other components via a slide or pivotable linkages.

An eighteenth aspect of the invention provides a method for fabricating a hydraulic or pneumatic microscale device, including: (a) forming a plurality of adhered layers of material, wherein the forming of each layer of material includes, (i) deposition of at least a first material; (ii) deposition of at least a second material; and (iii) planarization of the first and second materials to a common level; (b) removing of at least a portion of the first or second material from a plurality of layers after formation of the plurality of layers; (c) removing at least one of the first or second materials from a plurality of layers after formation of the plurality of adhered layers; (d) forming an o-ring between the two components of the device by bulging a flowable material though an orifice in at least one of the components; wherein the device includes: (i) a device body including an inlet for receiving a fluid flow and a passage for directing the fluid flow along a desired path through the body; (ii) an actuation mechanism functionally connected to the fluid flow path which undergoes a desired mechanical movement in response to fluid flow in the passage; wherein the device includes multiple components, at least one of which can move relative to the other components via a slide or pivotable linkages.

A nineteenth aspect of the invention provides a method for fabricating a hydraulic or pneumatic microscale device, including: (a) forming a plurality of adhered layers of material, wherein the forming of each layer of material includes, (i) deposition of at least a first material; (ii) deposition of at least a second material; and (iii) planarization of the first and second materials to a common level; (b) removing of at least a portion of the first or second material from a plurality of layers after formation of the plurality of layers; wherein the device includes: (i) a device body including an inlet for receiving a fluid flow and a passage for directing the fluid flow along a desired path through the body; (ii) an actuation mechanism functionally connected to the fluid flow path which undergoes a desired mechanical movement in response to fluid flow in the passage; wherein the device further includes at least a piston, a piston ring and a piston cylinder, wherein the piston and piston ring are formed in a position separated from that of a working range of the piston cylinder and thereafter the piston, piston ring are slid along a progressively narrowing surface into the a working range of the cylinder such that the piston ring is compressed.

A twentieth aspect of the invention provides a method for fabricating a hydraulic or pneumatic microscale device, including: (a) forming a plurality of adhered layers of material, wherein the forming of each layer of material includes, (i) deposition of at least a first material; (ii) deposition of at least a second material; and (iii) planarization of the first and second materials to a common level; (b) removing of at least a portion of the first or second material from a plurality of layers after formation of the plurality of layers; wherein the device includes at least 1st & 2nd portions of an actuation mechanism and where a fabrication position for the 1st & 2nd portions provide a spacing at least as large as a minimum feature size (MFS); and where a working range for relative movement of the 1st & 2nd portions during normal operation is displaced from a fabrication position, and where the 1st and 2nd portions are inhibited from returning to the fabrication position (e.g. by a releasable catch), and where the 1st & 2nd portions move relative to each other in at least a portion of the working range with the spacing between them less than an MFS.

A twenty-first aspect of the invention provides a method for fabricating a hydraulic or pneumatic microscale device, including: (a) forming a plurality of adhered layers of material, wherein the forming of each layer of material includes, (i) deposition of at least a first material; (ii) deposition of at least a second material; and (iii) planarization of the first and second materials to a common level; (b) removing of at least a portion of the first or second material from a plurality of layers after formation of the plurality of layers; wherein the device includes at least a 1st & 2nd portions of an actuation mechanism, and where a pair of surfaces around which portions of the mechanism move past one another during normal operation having an effective spacing less than an MFS during normal operation but which are separated by more than the MFS on individual layers during fabrication, and where a fabrication position and normal operation range overlap.

A twenty-second aspect of the invention provides a method for fabricating a hydraulic or pneumatic microscale device, including: (a) forming a plurality of adhered layers of material, wherein the forming of each layer of material includes, (i) deposition of at least a first material; (ii) deposition of at least a second material; and (iii) planarization of the first and second materials to a common level; (b) removing of at least a portion of the first or second material from a plurality of layers after formation of the plurality of layers; wherein the device includes at least a 1st & 2nd portions of an actuation mechanism that converts fluid flow into a desired mechanical movement and includes a compliant mechanism for at least partially closing gaps between components when transitioning from a loading position to a working range of the device wherein the gaps before transition are at least one layer thickness in the vertical dimension or are larger than an MFS in horizontal planes during fabrication and are, at least in part, within one layer in the vertical and/or smaller than the MFS when in the working range.

Variations of the sixteenth to twenty-first aspects of the invention are possible and may include, for example, one or more of the following:(1) the first portion of the actuation mechanism is inhibited by one or more mechanical components from returning to the fabrication position during normal operation of the device; (2) relative movement between two elements of the device occurs at an interference bushing; (3) relative movement between two elements of the device occurs at a linear checkerboard bushing; (4) relative movement between two elements of the device occur at a cylindrical checkerboard bushing; (5) a fluid outlet that is different from the fluid inlet; (6) the device is a hydraulic device; (7) the device is a medical device for insertion into a body of a patient during a minimally invasive procedure wherein the device provides or aids in the providing a diagnostic evaluation of, therapeutic treatment on, or preventive treatment on the body of a patient; and/or (8) the device is a pneumatic device.

Other aspects of the invention will be understood by those of skill in the art upon review of the teachings herein. Other aspects of the invention may involve combinations of the above noted aspects of the invention. These other aspects of the invention may provide various combinations of the aspects presented above as well as provide other configurations, structures, functional relationships, and processes that have not been specifically set forth above.

BRIEF DESCRIPTION OF THE DRAWINGS

FIGS. 2A-2F schematically depict side views of various stages of an electrochemical fabrication process as applied to the formation of a particular structure where a sacrificial material is selectively deposited while a structural material is blanket deposited.

FIGS. 5A-17 provide various views of a first embodiment of the invention that provides a hydraulic scissors example.

FIGS. 26A-26B provide views of a hydraulic or pneumatic actuator of a third embodiment of the invention that provides a viscous drag rotary actuator that includes a tool in the form of a saw blade.

FIGS. 27E-27F provide views of a fifth variation of the fourth embodiment of the invention that provides a pneumatic rotary actuator that includes a tool in the form of a saw blade.

DETAILED DESCRIPTION OF PREFERRED EMBODIMENTS

Electrochemical Fabrication in General

FIGS. 1A-1G, 2A-2F, and 3A-3C illustrate various features of one form of electrochemical fabrication. Other electrochemical fabrication techniques are set forth in the '630 patent referenced above, in the various previously incorporated publications, in various other patents and patent applications incorporated herein by reference. Still others may be derived from combinations of various approaches described in these publications, patents, and applications, or are otherwise known or ascertainable by those of skill in the art from the teachings set forth herein. All of these techniques may be combined with those of the various embodiments of various aspects of the invention to yield enhanced embodiments. Still other embodiments may be derived from combinations of the various embodiments explicitly set forth herein.

Figure 1A:
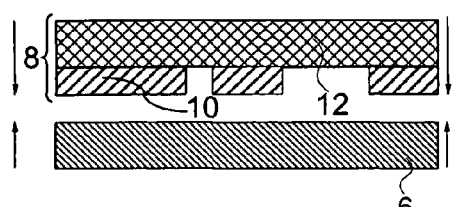
FIGS. 1A-1C schematically depict side views of various stages of a CC mask plating process, while FIGS. 1D-G schematically depict a side views of various stages of a CC mask plating process using a different type of CC mask.
Figure 1B:
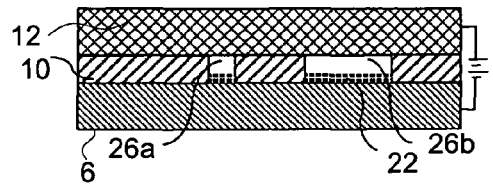
Figure 1C:
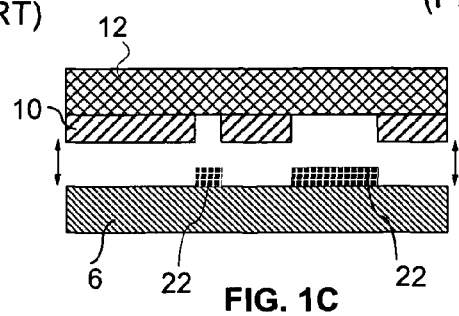
Figure 1D:
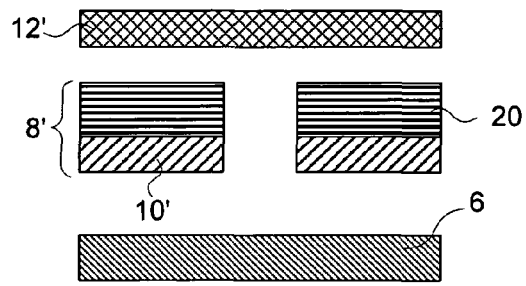
Figure 1E:
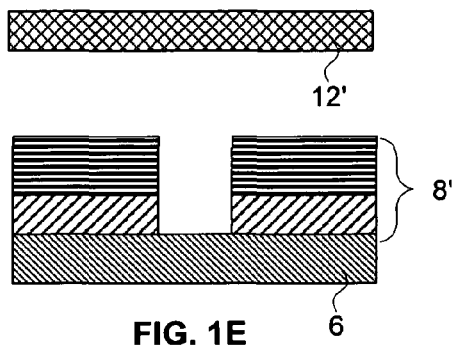
Figure 1F:
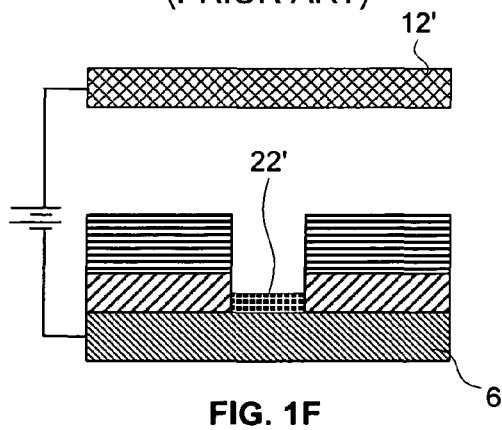
Figure 1G:
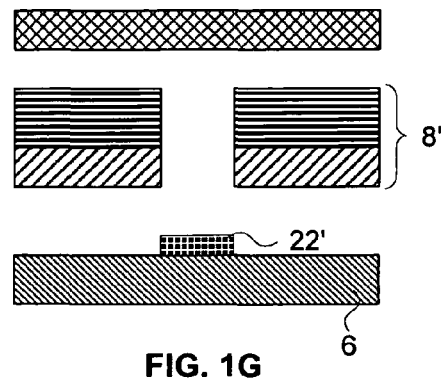
Figure 3A:
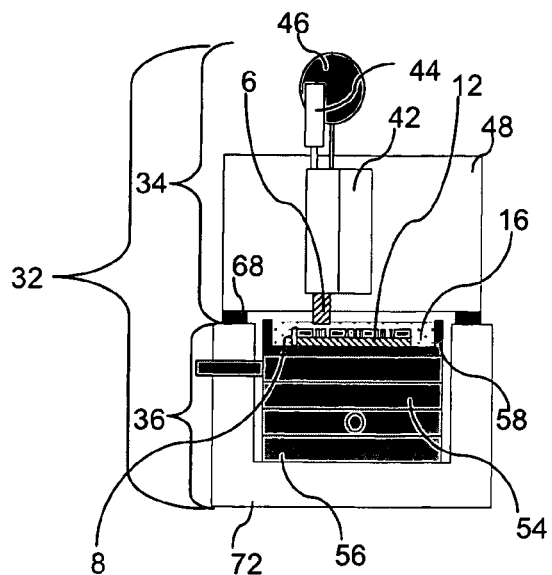
FIGS. 3A-3C schematically depict side views of various example subassemblies that may be used in manually implementing the electrochemical fabrication method depicted in FIGS. 2A-2F.
Figure 3B:
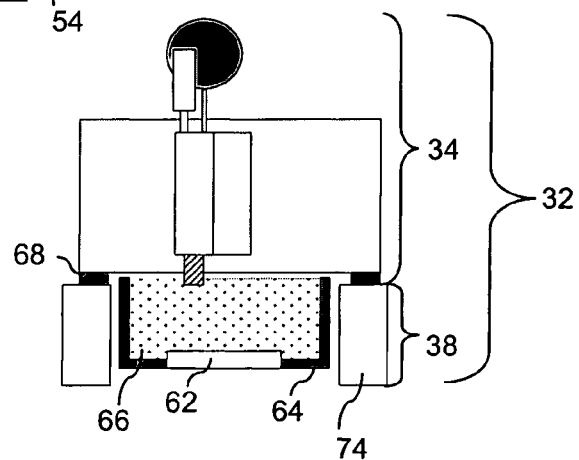
Figure 3C:
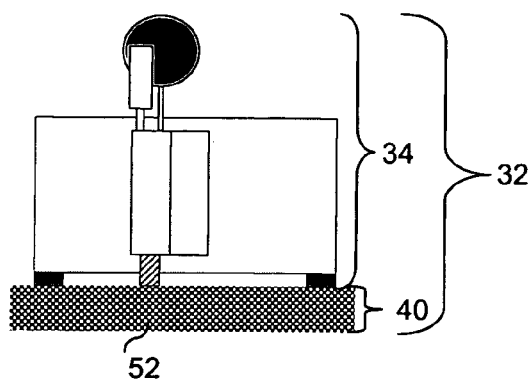
Figure 4A:
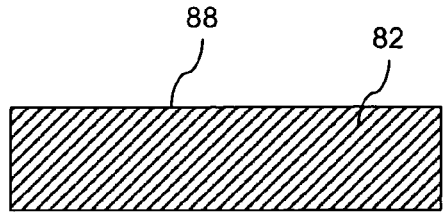
FIGS. 4A-4F schematically depict the formation of a first layer of a structure using adhered mask plating where the blanket deposition of a second material overlays both the openings between deposition locations of a first material and the first material itself
Figure 4B:
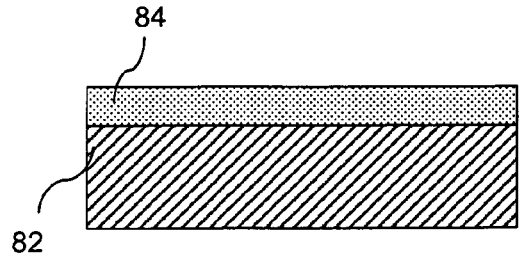
Figure 4C:
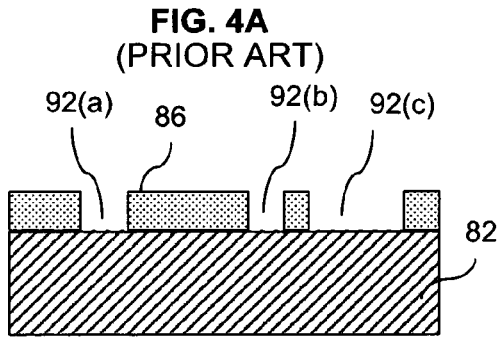
Figure 4D:
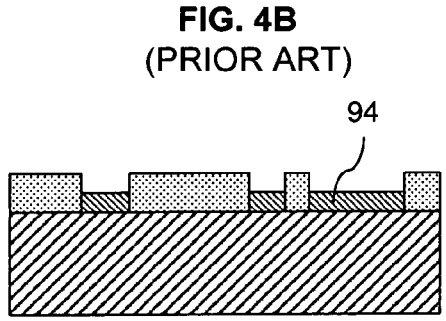
Figure 4E:
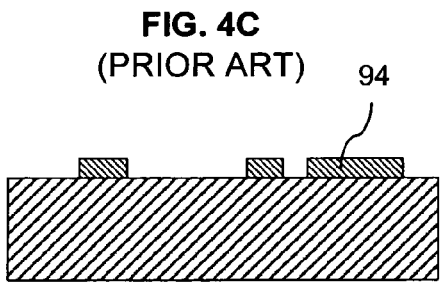
Figure 4F:
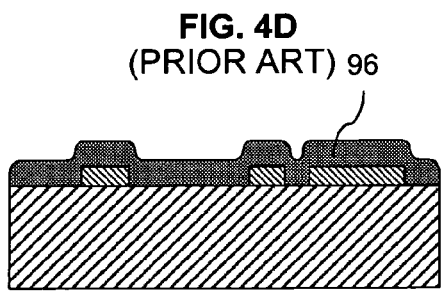
Figure 4G:
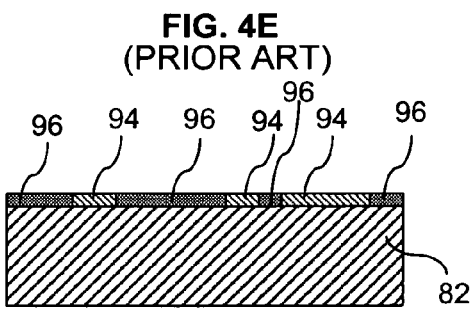
FIG. 4G depicts the completion of formation of the first layer resulting from planarizing the deposited materials to a desired level.
Figure 4H:
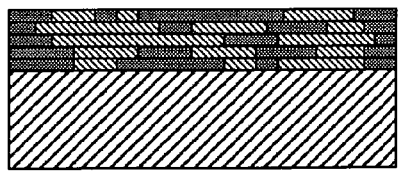
FIGS. 4H and 4I respectively depict the state of the process after formation of the multiple layers of the structure and after release of the structure from the sacrificial material.
Figure 4I:
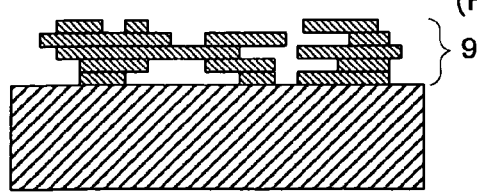

FIGS. 4A-4I illustrate various stages in the formation of a single layer of a multi-layer fabrication process where a second metal is deposited on a first metal as well as in openings in the first metal so that the first and second metal form part of the layer. In FIG. 4A a side view of a substrate 82 is shown, onto which patternable photoresist 84 is cast as shown in FIG. 4B. In FIG. 4C, a pattern of resist is shown that results from the curing, exposing, and developing of the resist. The patterning of the photoresist 84 results in openings or apertures 92(a)-92(c) extending from a surface 86 of the photoresist through the thickness of the photoresist to surface 88 of the substrate 82. In FIG. 4D a metal 94 (e.g. nickel) is shown as having been electroplated into the openings 92(a)-92(c). In FIG. 4E the photoresist has been removed (i.e. chemically stripped) from the substrate to expose regions of the substrate 82 which are not covered with the first metal 94. In FIG. 4F a second metal 96 (e.g. silver) is shown as having been blanket electroplated over the entire exposed portions of the substrate 82 (which is conductive) and over the first metal 94 (which is also conductive). FIG. 4G depicts the completed first layer of the structure which has resulted from the planarization of the first and second metals down to a height that exposes the first metal and sets a thickness for the first layer. In FIG. 4H the result of repeating the process steps shown in FIGS. 4B-4G several times to form a multi-layer structure are shown where each layer consists of two materials. For most applications, one of these materials is removed as shown in FIG. 4I to yield a desired 3-D structure 98 (e.g. component or device).

Various embodiments of various aspects of the invention are directed to formation of three-dimensional structures from materials some of which may be electrodeposited or electroless deposited. Some of these structures may be formed form a single build level formed from one or more deposited materials while others are formed from a plurality of build layers each including at least two materials (e.g. two or more layers, more preferably five or more layers, and most preferably ten or more layers). In some embodiments, layer thicknesses may be as small as one micron or as large as fifty microns. In other embodiments, thinner layers may be used while in other embodiments, thicker layers may be used. In some embodiments structures having features positioned with micron level precision and minimum features size on the order of tens of microns are to be formed. In other embodiments structures with less precise feature placement and/or larger minimum features may be formed. In still other embodiments, higher precision and smaller minimum feature sizes may be desirable. In the present application meso-scale and millimeter-scale have the same meaning and refer to devices that may have one or more dimensions extending into the 0.5-20 millimeter range, or somewhat larger, and with features positioned with precision in the 10-100 micron range and with minimum feature size on the order of 100 microns.

The various embodiments, alternatives, and techniques disclosed herein may form multi-layer structures using a single patterning technique on all layers or using different patterning techniques on different layers. For example, Various embodiments of the invention may perform selective patterning operations using conformable contact masks and masking operations (i.e. operations that use masks which are contacted to but not adhered to a substrate), proximity masks and masking operations (i.e. operations that use masks that at least partially selectively shield a substrate by their proximity to the substrate even if contact is not made), non-conformable masks and masking operations (i.e. masks and operations based on masks whose contact surfaces are not significantly conformable), and/or adhered masks and masking operations (masks and operations that use masks that are adhered to a substrate onto which selective deposition or etching is to occur as opposed to only being contacted to it). Conformable contact masks, proximity masks, and non-conformable contact masks share the property that they are preformed and brought to, or in proximity to, a surface which is to be treated (i.e. the exposed portions of the surface are to be treated). These masks can generally be removed without damaging the mask or the surface that received treatment to which they were contacted, or located in proximity to. Adhered masks are generally formed on the surface to be treated (i.e. the portion of that surface that is to be masked) and bonded to that surface such that they cannot be separated from that surface without being completely destroyed damaged beyond any point of reuse. Adhered masks may be formed in a number of ways including (1) by application of a photoresist, selective exposure of the photoresist, and then development of the photoresist, (2) selective transfer of pre-patterned masking material, and/or (3) direct formation of masks from computer controlled depositions of material.

Patterning operations may be used in selectively depositing material and/or may be used in the selective etching of material. Selectively etched regions may be selectively filled in or filled in via blanket deposition, or the like, with a different desired material. In some embodiments, the layer-by-layer build up may involve the simultaneous formation of portions of multiple layers. In some embodiments, depositions made in association with some layer levels may result in depositions to regions associated with other layer levels (i.e. regions that lie within the top and bottom boundary levels that define a different layer's geometric configuration). Such use of selective etching and interlaced material deposition in association with multiple layers is described in U.S. patent application Ser. No. 10/434,519, by Smalley, and entitled "Methods of and Apparatus for Electrochemically Fabricating Structures Via Interlaced Layers or Via Selective Etching and Filling of Voids layer elements" which is hereby incorporated herein by reference as if set forth in full.

Temporary substrates on which structures may be formed may be of the sacrificial-type (i.e. destroyed or damaged during separation of deposited materials to the extent they can not be reused), non-sacrificial-type (i.e. not destroyed or excessively damaged, i.e. not damaged to the extent they may not be reused, e.g. with a sacrificial or release layer located between the substrate and the initial layers of a structure that is formed). Non-sacrificial substrates may be considered reusable, with little or no rework (e.g. replanarizing one or more selected surfaces or applying a release layer, and the like) though they may or may not be reused for a variety of reasons.

DEFINITIONS

This section of the specification is intended to set forth definitions for a number of specific terms that may be useful in describing the subject matter of the various embodiments of the invention. It is believed that the meanings of most if not all of these terms is clear from their general use in the specification but they are set forth hereinafter to remove any ambiguity that may exist. It is intended that these definitions be used in understanding the scope and limits of any claims that use these specific terms. As far as interpretation of the claims of this patent disclosure are concerned, it is intended that these definitions take presence over any contradictory definitions or allusions found in any materials which are incorporated herein by reference.

"Build" as used herein refers, as a verb, to the process of building a desired structure or plurality of structures from a plurality of applied or deposited materials which are stacked and adhered upon application or deposition or, as a noun, to the physical structure or structures formed from such a process. Depending on the context in which the term is used, such physical structures may include a desired structure embedded within a sacrificial material or may include only desired physical structures which may be separated from one another or may require dicing and/or slicing to cause separation.

"Build axis" or "build orientation" is the axis or orientation that is substantially perpendicular to substantially planar levels of deposited or applied materials that are used in building up a structure. The planar levels of deposited or applied materials may be or may not be completely planar but are substantially so in that the overall extent of their cross-sectional dimensions are significantly greater than the height of any individual deposit or application of material (e.g. 100, 500, 1000, 5000, or more times greater). The planar nature of the deposited or applied materials may come about from use of a process that leads to planar deposits or it may result from a planarization process (e.g. a process that includes mechanical abrasion, e.g. lapping, fly cutting, grinding, or the like) that is used to remove material regions of excess height. Unless explicitly noted otherwise, "vertical" as used herein refers to the build axis or nominal build axis (if the layers are not stacking with perfect registration) while "horizontal" refers to a direction within the plane of the layers (i.e. the plane that is substantially perpendicular to the build axis).

"Build layer" or "layer of structure" as used herein does not refer to a deposit of a specific material but instead refers to a region of a build located between a lower boundary level and an upper boundary level which generally defines a single cross-section of a structure being formed or structures which are being formed in parallel. Depending on the details of the actual process used to form the structure, build layers are generally formed on and adhered to previously formed build layers. In some processes the boundaries between build layers are defined by planarization operations which result in successive build layers being formed on substantially planar upper surfaces of previously formed build layers. In some embodiments, the substantially planar upper surface of the preceding build layer may be textured to improve adhesion between the layers. In other build processes, openings may exist in or be formed in the upper surface of a previous but only partially formed build layers such that the openings in the previous build layers are filled with materials deposited in association with current build layers which will cause interlacing of build layers and material deposits. Such interlacing is described in U.S. patent application Ser. No. 10/434,519. This referenced application is incorporated herein by reference as if set forth in full. In most embodiments, a build layer includes at least one primary structural material and at least one primary sacrificial material. However, in some embodiments, two or more primary structural materials may used without a primary sacrificial material (e.g. when one primary structural material is a dielectric and the other is a conductive material). In some embodiments, build layers are distinguishable from each other by the source of the data that is used to yield patterns of the deposits, applications, and/or etchings of material that form the respective build layers. For example, data descriptive of a structure to be formed which is derived from data extracted from different vertical levels of a data representation of the structure define different build layers of the structure. The vertical separation of successive pairs of such descriptive data may define the thickness of build layers associated with the data. As used herein, at times, "build layer" may be loosely referred simply as "layer". In many embodiments, deposition thickness of primary structural or sacrificial materials (i.e. the thickness of any particular material after it is deposited) is generally greater than the layer thickness and a net deposit thickness is set via one or more planarization processes which may include, for example, mechanical abrasion (e.g. lapping, fly cutting, polishing, and the like) and/or chemical etching (e.g. using selective or non-selective etchants). The lower boundary and upper boundary for a build layer may be set and defined in different ways. From a design point of view they may be set based on a desired vertical resolution of the structure (which may vary with height). From a data manipulation point of view, the vertical layer boundaries may be defined as the vertical levels at which data descriptive of the structure is processed or the layer thickness may be defined as the height separating successive levels of cross-sectional data that dictate how the structure will be formed. From a fabrication point of view, depending on the exact fabrication process used, the upper and lower layer boundaries may be defined in a variety of different ways. For example by planarization levels or effective planarization levels (e.g. lapping levels, fly cutting levels, chemical mechanical polishing levels, mechanical polishing levels, vertical positions of structural and/or sacrificial materials after relatively uniform etch back following a mechanical or chemical mechanical planarization process). For example, by levels at which process steps or operations are repeated. At levels at which, at least theoretically, lateral extends of structural material can be changed to define new cross-sectional features of a structure.

"Layer thickness" is the height along the build axis between a lower boundary of a build layer and an upper boundary of that build layer.

"Planarization" is a process that tends to remove materials, above a desired plane, in a substantially non-selective manner such that all deposited materials are brought to a substantially common height or desired level (e.g. within 20%, 10%, 5%, or even 1% of a desired layer boundary level). For example, lapping removes material in a substantially non-selective manner though some amount of recession one material or another may occur (e.g. copper may recess relative to nickel). Planarization may occur primarily via mechanical means, e.g. lapping, grinding, fly cutting, milling, sanding, abrasive polishing, frictionally induced melting, other machining operations, or the like (i.e. mechanical planarization). Mechanical planarization maybe followed or proceeded by thermally induced planarization (.e.g. melting) or chemically induced planarization (e.g. etching). Planarization may occur primarily via a chemical and/or electrical means (e.g. chemical etching, electrochemical etching, or the like). Planarization may occur via a simultaneous combination of mechanical and chemical etching (e.g. chemical mechanical polishing (CMP)).

"Structural material" as used herein refers to a material that remains part of the structure when put into use.

"Supplemental structural material" as used herein refers to a material that forms part of the structure when the structure is put to use but is not added as part of the build layers but instead is added to a plurality of layers simultaneously (e.g. via one or more coating operations that applies the material, selectively or in a blanket fashion, to a one or more surfaces of a desired build structure that has been released from a sacrificial material.

"Primary structural material" as used herein is a structural material that forms part of a given build layer and which is typically deposited or applied during the formation of that build layer and which makes up more than 20% of the structural material volume of the given build layer. In some embodiments, the primary structural material may be the same on each of a plurality of build layers or it may be different on different build layers. In some embodiments, a given primary structural material may be formed from two or more materials by the alloying or diffusion of two or more materials to form a single material.

"Secondary structural material" as used herein is a structural material that forms part of a given build layer and is typically deposited or applied during the formation of the given build layer but is not a primary structural material as it individually accounts for only a small volume of the structural material associated with the given layer. A secondary structural material will account for less than 20% of the volume of the structural material associated with the given layer. In some preferred embodiments, each secondary structural material may account for less than 10%, 5%, or even 2% of the volume of the structural material associated with the given layer. Examples of secondary structural materials may include seed layer materials, adhesion layer materials, barrier layer materials (e.g. diffusion barrier material), and the like. These secondary structural materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931. In other embodiments, such coatings may be applied in a non-planar manner, for example, in openings in and over a patterned masking material that has been applied to previously planarized layers of material as taught in U.S. patent application Ser. No. 10/841,383. These referenced applications are incorporated herein by reference as if set forth in full herein.

"Functional structural material" as used herein is a structural material that would have been removed as a sacrificial material but for its actual or effective encapsulation by other structural materials. Effective encapsulation refers, for example, to the inability of an etchant to attack the functional structural material due to inaccessibility that results from a very small area of exposure and/or due to an elongated or tortuous exposure path. For example, large (10,000 $\mu m^2$) but thin (e.g. less than 0.5 microns) regions of sacrificial copper sandwiched between deposits of nickel may define regions of functional structural material depending on ability of a release etchant to remove the sandwiched copper.

"Sacrificial material" is material that forms part of a build layer but is not a structural material. Sacrificial material on a given build layer is separated from structural material on that build layer after formation of that build layer is completed and more generally is removed from a plurality of layers after completion of the formation of the plurality of layers during a "release" process that removes the bulk of the sacrificial material or materials. In general sacrificial material is located on a build layer during the formation of one, two, or more subsequent build layers and is thereafter removed in a manner that does not lead to a planarized surface. Materials that are applied primarily for masking purposes, i.e. to allow subsequent selective deposition or etching of a material, e.g. photoresist that is used in forming a build layer but does not form part of the build layer) or that exist as part of a build for less than one or two complete build layer formation cycles are not considered sacrificial materials as the term is used herein but instead shall be referred as masking materials or as temporary materials. These separation processes are sometimes referred to as a release process and may or may not involve the separation of structural material from a build substrate. In many embodiments, sacrificial material within a given build layer is not removed until all build layers making up the three-dimensional structure have been formed. Of course sacrificial material may be, and typically is, removed from above the upper level of a current build layer during planarization operations during the formation of the current build layer. Sacrificial material is typically removed via a chemical etching operation but in some embodiments may be removed via a melting operation or electrochemical etching operation. In typical structures, the removal of the sacrificial material (i.e. release of the structural material from the sacrificial material) does not result in planarized surfaces but instead results in surfaces that are dictated by the boundaries of structural materials located on each build layer. Sacrificial materials are typically distinct from structural materials by having different properties therefrom (e.g. chemical etchability, hardness, melting point, etc.) but in some cases, as noted previously, what would have been a sacrificial material may become a structural material by its actual or effective encapsulation by other structural materials. Similarly, structural materials may be used to form sacrificial structures that are separated from a desired structure during a release process via the sacrificial structures being only attached to sacrificial material or potentially by dissolution of the sacrificial structures themselves using a process that is insufficient to reach structural material that is intended to form part of a desired structure. It should be understood that in some embodiments, small amounts of structural material may be removed, after or during release of sacrificial material. Such small amounts of structural material may have been inadvertently formed due to imperfections in the fabrication process or may result from the proper application of the process but may result in features that are less than optimal (e.g. layers with stairs steps in regions where smooth sloped surfaces are desired. In such cases the volume of structural material removed is typically minuscule compared to the amount that is retained and thus such removal is ignored when labeling materials as sacrificial or structural. Sacrificial materials are typically removed by a dissolution process, or the like, that destroys the geometric configuration of the sacrificial material as it existed on the build layers. In many embodiments, the sacrificial material is a conductive material such as a metal. As will be discussed hereafter, masking materials though typically sacrificial in nature are not termed sacrificial materials herein unless they meet the required definition of sacrificial material.

"Supplemental sacrificial material" as used herein refers to a material that does not form part of the structure when the structure is put to use and is not added as part of the build layers but instead is added to a plurality of layers simultaneously (e.g. via one or more coating operations that applies the material, selectively or in a blanket fashion, to a one or more surfaces of a desired build structure that has been released from an initial sacrificial material. This supplemental sacrificial material will remain in place for a period of time and/or during the performance of certain post layer formation operations, e.g. to protect the structure that was released from a primary sacrificial material, but will be removed prior to putting the structure to use.

"Primary sacrificial material" as used herein is a sacrificial material that is located on a given build layer and which is typically deposited or applied during the formation of that build layer and which makes up more than 20% of the sacrificial material volume of the given build layer. In some embodiments, the primary sacrificial material may be the same on each of a plurality of build layers or may be different on different build layers. In some embodiments, a given primary sacrificial material may be formed from two or more materials by the alloying or diffusion of two or more materials to form a single material.

"Secondary sacrificial material" as used herein is a sacrificial material that is located on a given build layer and is typically deposited or applied during the formation of the build layer but is not a primary sacrificial materials as it individually accounts for only a small volume of the sacrificial material associated with the given layer. A secondary sacrificial material will account for less than 20% of the volume of the sacrificial material associated with the given layer. In some preferred embodiments, each secondary sacrificial material may account for less than 10%, 5%, or even 2% of the volume of the sacrificial material associated with the given layer. Examples of secondary structural materials may include seed layer materials, adhesion layer materials, barrier layer materials (e.g. diffusion barrier material), and the like. These secondary sacrificial materials are typically applied to form coatings having thicknesses less than 2 microns, 1 micron, 0.5 microns, or even 0.2 microns). The coatings may be applied in a conformal or directional manner (e.g. via CVD, PVD, electroless deposition, or the like). Such coatings may be applied in a blanket manner or in a selective manner. Such coatings may be applied in a planar manner (e.g. over previously planarized layers of material) as taught in U.S. patent application Ser. No. 10/607,931. In other embodiments, such coatings may be applied in a non-planar manner, for example, in openings in and over a patterned masking material that has been applied to previously planarized layers of material as taught in U.S. patent application Ser. No. 10/841,383. These referenced applications are incorporated herein by reference as if set forth in full herein.

"Adhesion layer", "seed layer", "barrier layer", and the like refer to coatings of material that are thin in comparison to the layer thickness and thus generally form secondary structural material portions or sacrificial material portions of some layers. Such coatings may be applied uniformly over a previously formed build layer, they may be applied over a portion of a previously formed build layer and over patterned structural or sacrificial material existing on a current (i.e. partially formed) build layer so that a non-planar seed layer results, or they may be selectively applied to only certain locations on a previously formed build layer. In the event such coatings are non-selectively applied, selected portions may be removed (1) prior to depositing either a sacrificial material or structural material as part of a current layer or (2) prior to beginning formation of the next layer or they may remain in place through the layer build up process and then etched away after formation of a plurality of build layers.

"Masking material" is a material that may be used as a tool in the process of forming a build layer but does not form part of that build layer. Masking material is typically a photopolymer or photoresist material or other material that may be readily patterned. Masking material is typically a dielectric. Masking material, though typically sacrificial in nature, is not a sacrificial material as the term is used herein. Masking material is typically applied to a surface during the formation of a build layer for the purpose of allowing selective deposition, etching, or other treatment and is removed either during the process of forming that build layer or immediately after the formation of that build layer.

"Multilayer structures" are structures formed from multiple build layers of deposited or applied materials.

"Multilayer three-dimensional (or 3D or 3-D) structures" are Multilayer Structures that meet at least one of two criteria: (1) the structural material portion of at least two layers of which one has structural material portions that do not overlap structural material portions of the other.

"Complex multilayer three-dimensional (or 3D or 3-D) structures" are multilayer three-dimensional structures formed from at least three layers where a line may be defined that hypothetically extends vertically through at least some portion of the build layers of the structure will extend from structural material through sacrificial material and back through structural material or will extend from sacrificial material through structural material and back through sacrificial material (these might be termed vertically complex multilayer three-dimensional structures). Alternatively, complex multilayer three-dimensional structures may be defined as multilayer three-dimensional structures formed from at least two layers where a line may be defined that hypothetically extends horizontally through at least some portion of a build layer of the structure that will extend from structural material through sacrificial material and back through structural material or will extend from sacrificial material through structural material and back through sacrificial material (these might be termed horizontally complex multilayer three-dimensional structures). Worded another way, in complex multilayer three-dimensional structures, a vertically or horizontally extending hypothetical line will extend from one or structural material or void (when the sacrificial material is removed) to the other of void or structural material and then back to structural material or void as the line is traversed along at least a portion of the line.

"Moderately complex multilayer three-dimensional (or 3D or 3-D) structures are complex multilayer 3D structures for which the alternating of void and structure or structure and void not only exists along one of a vertically or horizontally extending line but along lines extending both vertically and horizontally.

"Highly complex multilayer (or 3D or 3-D) structures are complex multilayer 3D structures for which the structure-to-void-to-structure or void-to-structure-to-void alternating occurs once along the line but occurs a plurality of times along a definable horizontally or vertically extending line.

"Up-facing feature" is an element dictated by the cross-sectional data for a given build layer "n" and a next build layer "n+1" that is to be formed from a given material that exists on the build layer "n" but does not exist on the immediately succeeding build layer "n+1". For convenience the term "up-facing feature" will apply to such features regardless of the build orientation.

"Down-facing feature" is an element dictated by the cross-sectional data for a given build layer "n" and a preceding build layer "n−1" that is to be formed from a given material that exists on build layer "n" but does not exist on the immediately preceding build layer "n−1". As with up-facing features, the term "down-facing feature" shall apply to such features regardless of the actual build orientation.

"Continuing region" is the portion of a given build layer "n" that is dictated by the cross-sectional data for the given build layer "n", a next build layer "n+1" and a preceding build layer "n−1" that is neither up-facing nor down-facing for the build layer "n".

"Minimum feature size" refers to a necessary or desirable spacing between structural material elements on a given layer that are to remain distinct in the final device configuration. If the minimum feature size is not maintained on a given layer, the fabrication process may result in structural material inadvertently bridging the two structural elements due to masking material failure or failure to appropriately fill voids with sacrificial material during formation of the given layer such that during formation of a subsequent layer structural material inadvertently fills the void. More care during fabrication can lead to a reduction in minimum feature size or a willingness to accept greater losses in productivity can result in a decrease in the minimum feature size. However, during fabrication for a given set of process parameters, inspection diligence, and yield (successful level of production) a minimum design feature size is set in one way or another. The above described minimum feature size may more appropriately be termed minimum feature size of sacrificial material regions. Conversely a minimum feature size for structure material regions (minimum width or length of structural material elements) may be specified. Depending on the fabrication method and order of deposition of structural material and sacrificial material, the two types of minimum feature sizes may be different. In practice, for example, using electrochemical fabrication methods and described herein, the minimum features size on a given layer may be roughly set to a value that approximates the layer thickness used to form the layer and it may be considered the same for both structural and sacrificial material widths and lengths. In some more rigorously implemented processes, examination regiments, and rework requirements, it may be set to an amount that is 80%, 50%, or even 30% of the layer thickness. Other values or methods of setting minimum feature sizes may be set.

Minimally Invasive Surgery or Procedures:

Various devices set forth in the embodiments of the invention may be used in the performance of medical procedure and particularly in the performance of procedures where very small tools are need. Such procedures include various minimally invasive procedures where access to a desired working location in the body of a patient occurs via one or more lumens inserted through the skin or through a body cavity where tools, materials, and observations devices are inserted via the lumen(s). In some such procedures access to a desired location may be along a tortuous path. As used herein "tortuous path" refers to a path taken by the lumen which has turns or other obstacles which are numerous and/or sharp such a that controlled and reliable manipulation of a tool or device at the distal end of the lumen via push tubes, pull wires, rotating cables, or the like, to achieve desired functions from manipulations at the proximal end of the lumen(s) is not achievable or at least not readily achievable by operators (surgeons, interventionalists, etc.) having reasonable skills and within reasonable or desirable time constraints and within reasonable risk limits.

Embodiment 1

Hydraulic Scissors

FIGS. 5A-17 provide various views of a first embodiment of the invention that provides a hydraulic scissors example. When forming the device via multi-layer, multi-material electrochemical fabrication methods it is preferred that the device be fabricated on its so as to minimize the number of layers used in forming it as well as to take advantage of the processes ability to form smooth curves in the planes of layers.

FIG. 5A provides a top perspective view of the hydraulic scissors 100 of the present embodiment while FIG. 5B provides a bottom perspective view of the scissors. The scissors possess a distal end 194 and a proximal end 192. According to this embodiment the scissor have a fixed blade 104 and a movable blade 106 connected together by a pivot 118 (e.g. a ¼ turn pin or connector as illustrated) that includes a slotted flat head on the upper side and an elongated base on the bottom side. The elongated base is configured to pass through the moving and fixed blades and to engage an complementary recess on the backside of the fixed blade after insertion and rotating the pin a ¼ turn. The moving blade also includes, near the pivot point, a side extension 108 that includes a hole for engaging a distal end of a spring 110. The side extension may also function, in combination with the body, or housing 102, of the hydraulic mechanism, as a stop that limits the opening angle between the blades. The moveable blade may also be fitted with one or more physical stops which could limit the overlap limit and opening limits of the blades. A catch head extending into notch 120 in the housing sets the working range for piston movement and sets the distal extension limit of the piston when fluid is applied to the cylinder thus ensuring that the piston does extend beyond its working range within the cylinder. The spring also includes a proximal end that attaches to a proximal extension on the body of the housing 102. The proximal end of the housing also includes a hydraulic fluid inlet 112 and a hole 114 for accepting a handle (e.g. in the form of a wire).

Figure 6:
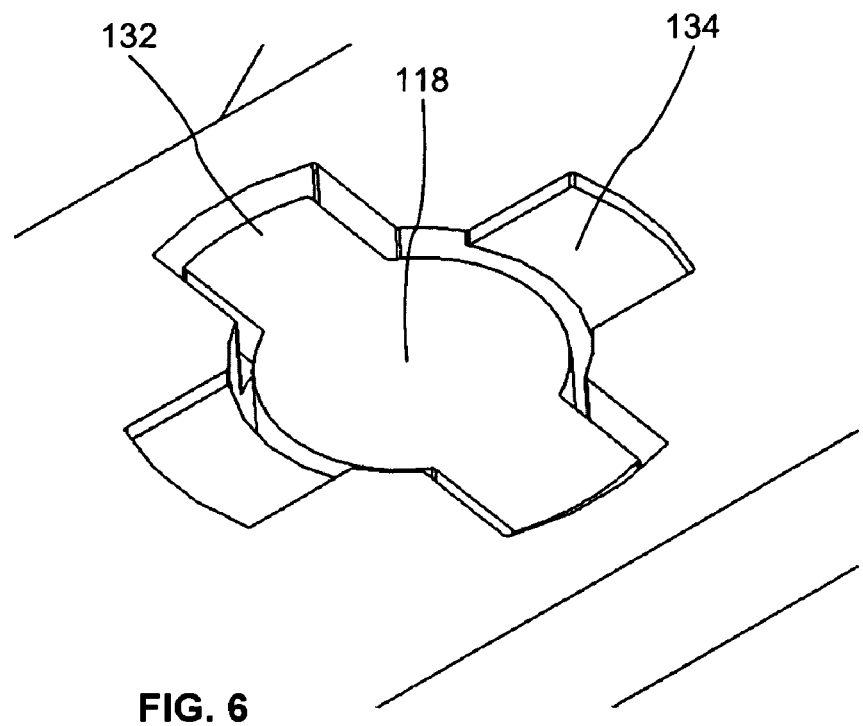

FIG. 6 provides a close up perspective view of the back side of the ¼ turn pin 118 as it is located in the opening in the fixed blade but has not been pushed in far enough (high enough to exit the deep recess to turn so that it may be locked into the shallow recess 134.

Figure 7:
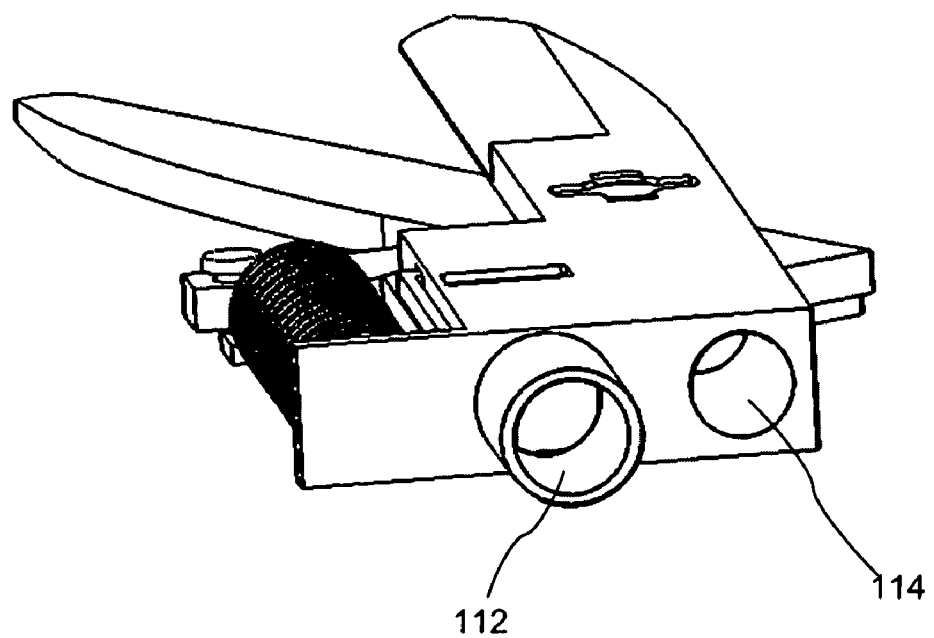

FIG. 7 provides a perspective view of the scissors of FIGS. 5A and 5B from the proximal end so that the fluid inlet passage 112 and hole 114 for the handle can be seen.

Figure 8:
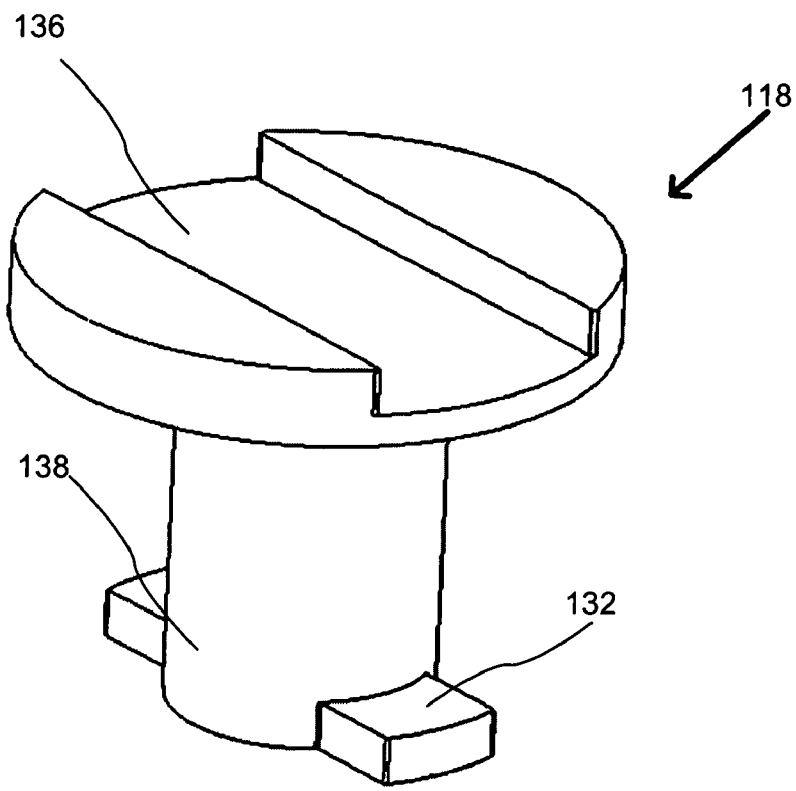

FIG. 8 provides a perspective view of the ¼ turn pin 118 showing the head containing the screwdriver slot 136, the shaft 138 and the elongated base element (i.e. the tabs 132 extending out of the base of the shaft. In some alternative embodiments, a different pin configuration or even screw configuration can be used to provide a pivot and to hold the blades against one another.

Figure 9:
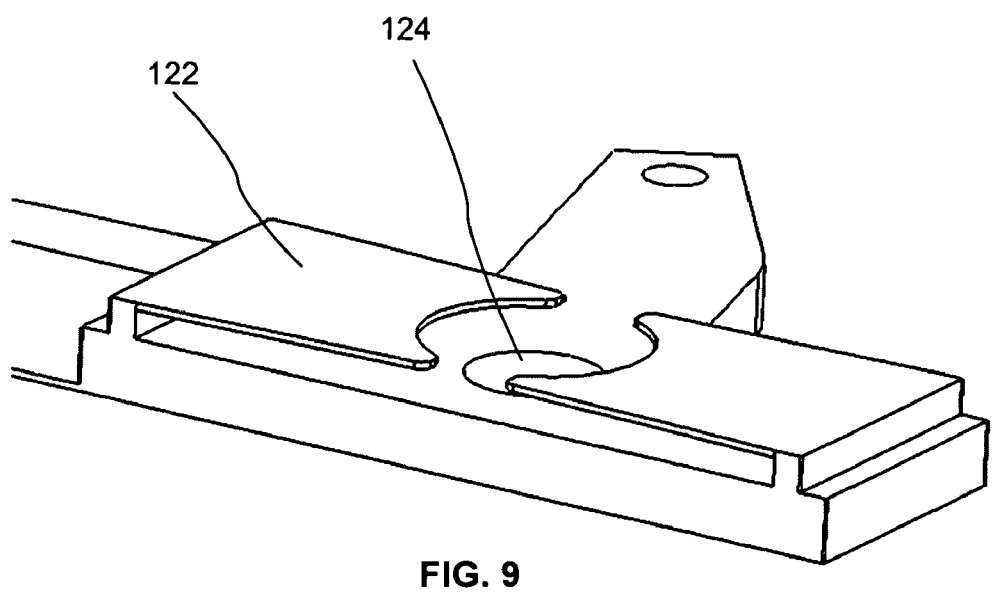
Figure 10:
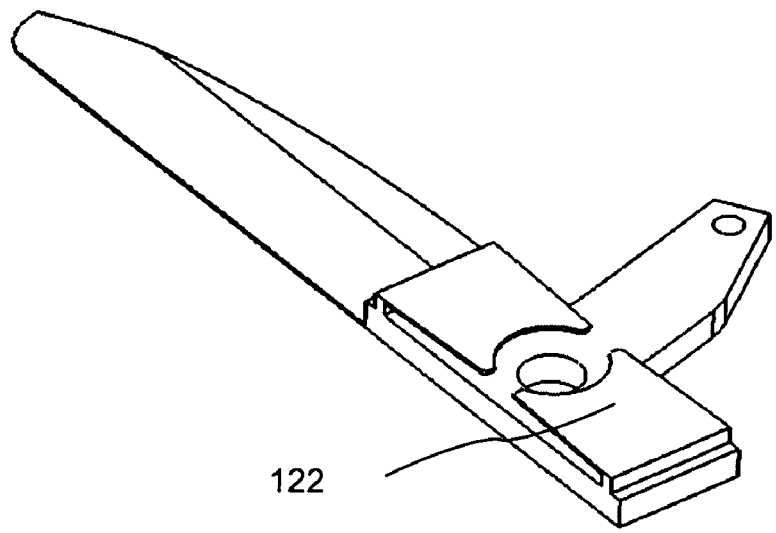

FIG. 9 depicts a close up of the upper portion of the movable blade in proximity to the pivot while FIG. 10 depicts a slightly different perspective of the entire moveable blade. As can be seen the upper surface includes a pair of flexures 122 (i.e. leaf springs as depicted) that will abut the lower surface of the head of the pin to bias it upward once it is turned into its locking position. In some alternative embodiments where the pin is formed separate from the blades, it is necessary to insert the pin through the moveable blade hole 124, and in such cases, the blade may include notches for passing the tabs on the pin. In such alternatives, the notches may be provided with any appropriate orientation.

Figure 11:
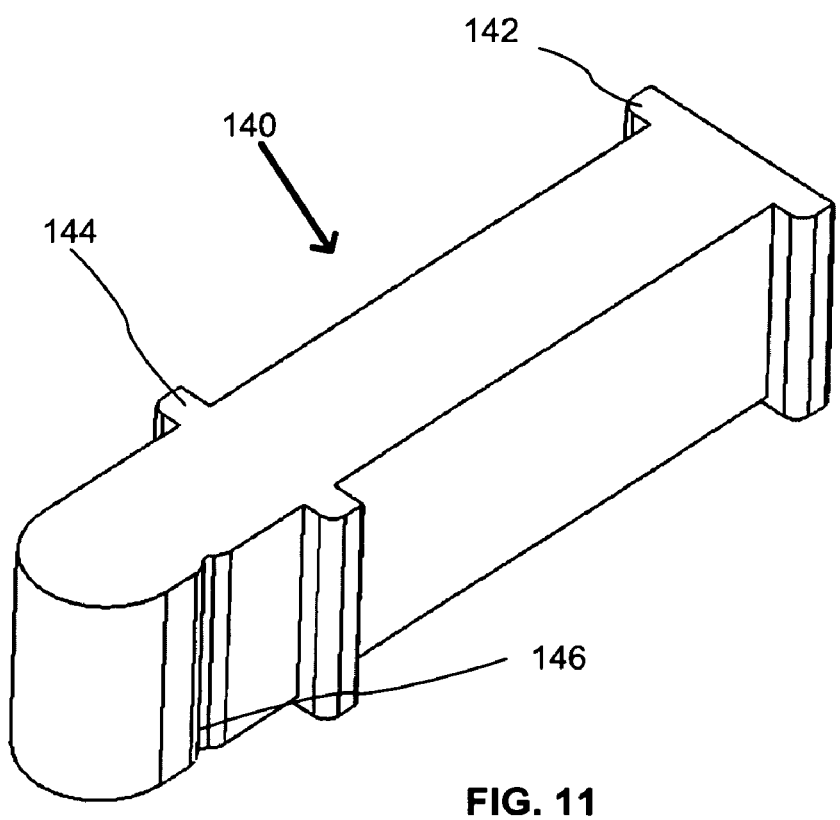
Figure 12:
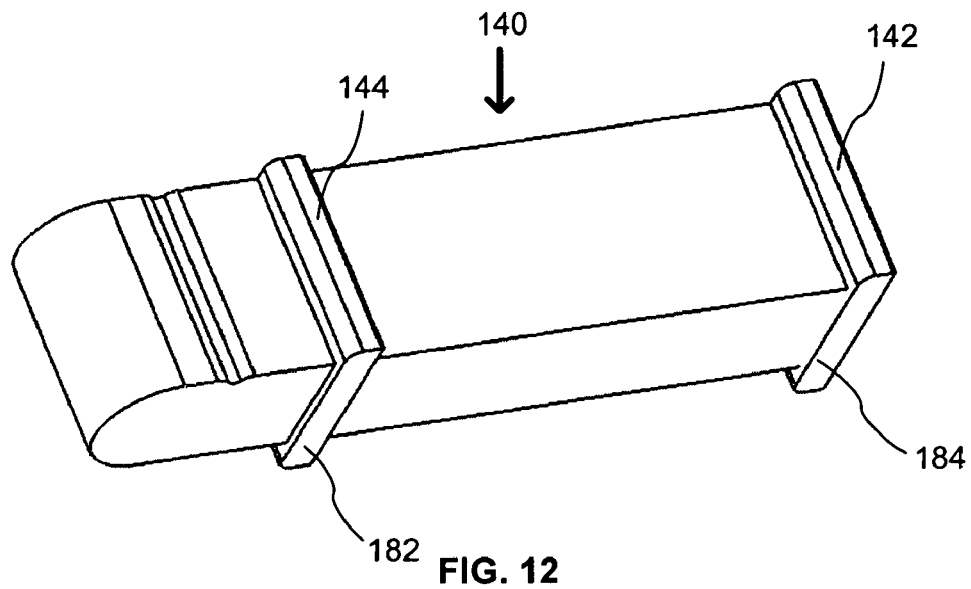

FIGS. 11 and 12 provide perspective views of the hydraulic piston 140 used within a cylinder of the housing to receive the hydraulic fluid pressure and to translate the fluid pressure into mechanical movement of the moveable blade via contact between the distal end of the piston and the proximal extension of the moveable blade. As can be seen the distal end of the piston has a rounded surface to avoid non-uniformities of contact between the piston and the extension at different levels of the piston extension. As can be in FIGS. 11 and 12 the piston includes distal tab 144 and proximal tab 142 for making the piston wider so as to allow it to come into closer proximity to the walls of the cylinder after it is fabricated and loaded into a position that is somewhat distal compared to it position during fabrication. In the present embodiment, it is preferred that the piston be fabricated within the cylinder though in other embodiments, the piston may be fabricated separately along with other components and then the device assembled. In FIGS. 11 and 12, both the distal and proximal tabs are shown as having sloped distal surfaces that help ensure non-binding motion occurs in the distal direction while the proximal side of the tabs are shown without such slopes. In some alternative embodiments, slopes may also exist on the proximal sides of the tabs. In still other alternative embodiments, proximal and/or distal tabs may occur in groups (e.g. closely spaced groups). In other embodiments, similar notches 146 and tabs may be provided on the top 184 and bottom surfaces of the piston though such additional notches and tabs may not be necessary as it may be possible to form thin layers that do not include structural material immediately below or above the piston. These gaps immediately below the bottom of the piston and immediate above the top of the piston may be made as thin as desired to directly provide desired clearances. If such clearances are not possible due to difficulties in removing sacrificial material, the use of tabs may be helpful and potentially may be used in combination with relatively thin layers immediately below and above the tabs.

Figure 13:
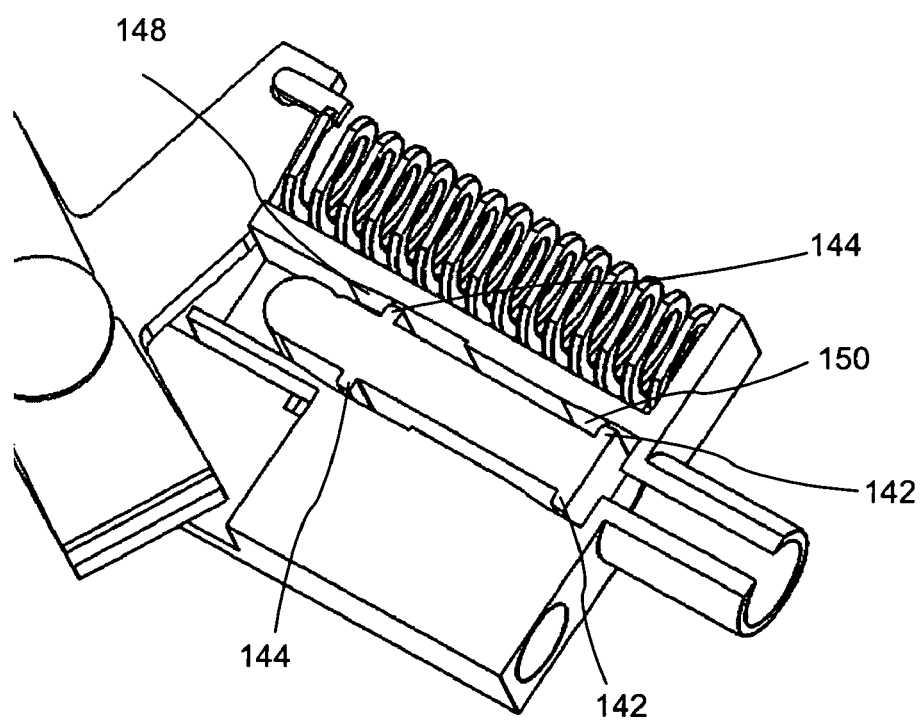

FIG. 13 provides a cross-sectional perspective view of the housing with the top cut away so the piston and cylinder shape can be seen. As noted above the piston includes proximal tab 142 and distal tab 144 and when the piston is located at its most proximal position (i.e. slightly spaced from the inner proximal wall of the cylinder), the tabs are located within regions 148 and 150 of the cylinder which have increased width. These regions of increased width give way to regions of narrower width as the piston is moved distally. The cylinder is provided with sloped regions that transition from the larger width to the smaller width which provide for a smooth transition and thus minimization of the possibility of piston and cylinder binding. The regions of wider cross-sectional width provide the space required to allow minimum feature size limitations to be met during fabrication while the narrower regions provide close enough tolerance to allow effective actuation.

Figure 14:
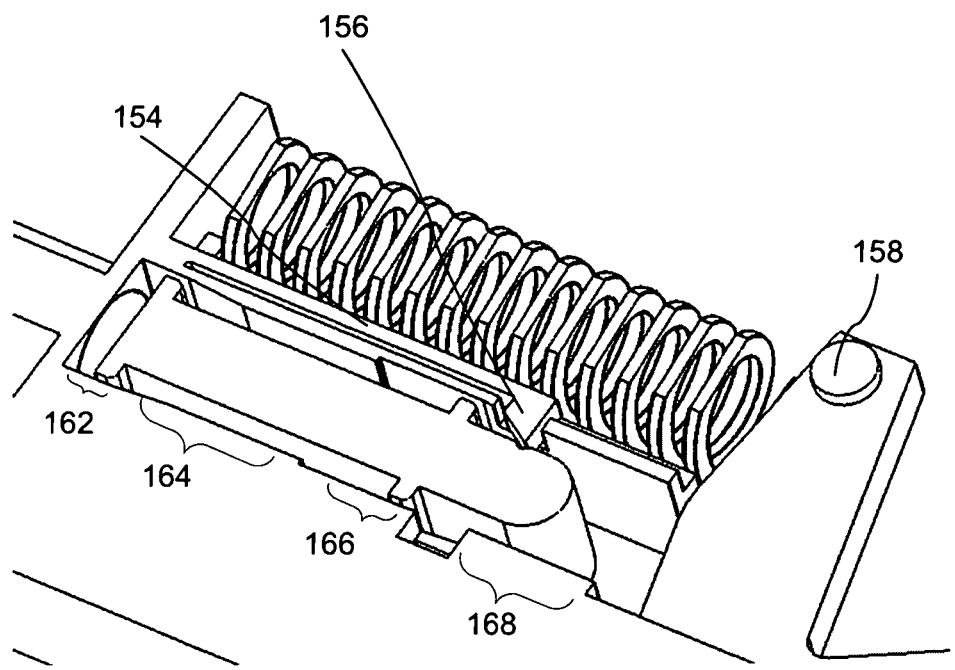

FIG. 14 provides a cross-sectional perspective view from the bottom side of the device so that the bottom portion of the cylinder and piston can be seen. FIG. 14 illustrates a mechanism for ensuring that after formation and initial movement of the piston to a working location it will not inadvertently move back to its fabrication position (i.e. to a position that places the tabs on the piston in the vicinity of the wider regions of the cylinder). Fabrication regions 162 and 166 and working regions 164 and 168 for both the proximal and distal tabs are illustrated in the figure with bracketing. In FIG. 14 the piston is located in its as formed position with a catch head 156 located at the distal end of a flexure (together this element is simply referred to as the catch 154) and with the tip of the catch head located in a notch in the side of the piston via hole 120. In some alternatives, a notch may exist on the opposite side of the piston along with a second catch. The spacing between the catch head tip and the notched wall of the piston is preferably greater than or equal to the minimum feature size. After formation, an initial distal movement of the piston will push the distal tab(s) beyond the catch head. After release of the piston from its initial distal movement, the piston will be inhibited from moving proximally back to its initial position by the blockage provided by the flat faces of the proximal side of the distal tab and the distal side of the catch head (i.e. faces which are perpendicular to the primary motion of the piston). In some embodiments one or both of these surfaces may have reentrant angles that provide even further inhibition against inadvertent back motion of the piston to its formation position. In some embodiments, a release for the catch head may exist which could be used to allow the piston to move back to its original (i.e. as fabricated position).

Figure 15:
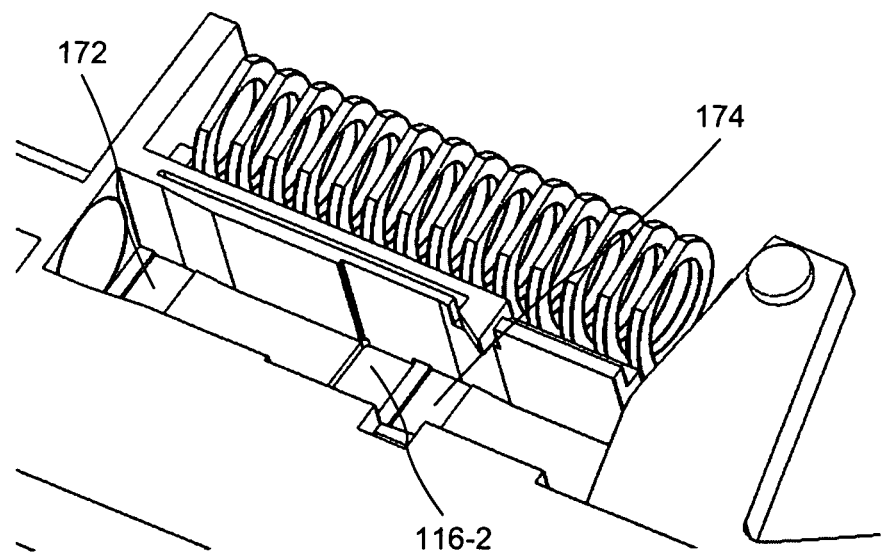

FIG. 15 provides a cross-sectional perspective view similar to that of FIG. 14 with the exception that the piston is removed so that notches 172 and 174 tabs in the upper cylinder surface can be seen. In some alternative embodiments, similar notching on the lower cylinder wall is also possible and tabs on the lower surface of the piston are also possible.

Figure 16:
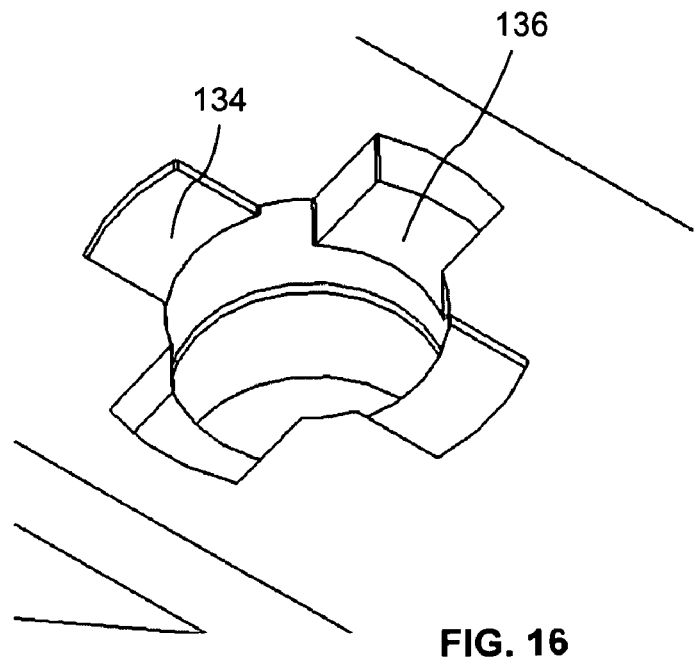

FIG. 16 provides a close up perspective view of the back side of the fixed blade similar to that shown in FIG. 6 with the exception of the pin has been removed. During formation, the tabs on the ¼ turn pin are located within the region defined by the deep recesses 136 so that they may be formed with appropriate clearances and are turned to catch against the blade in the shallow recess 134 regions before putting the scissors to use.

Figure 17:
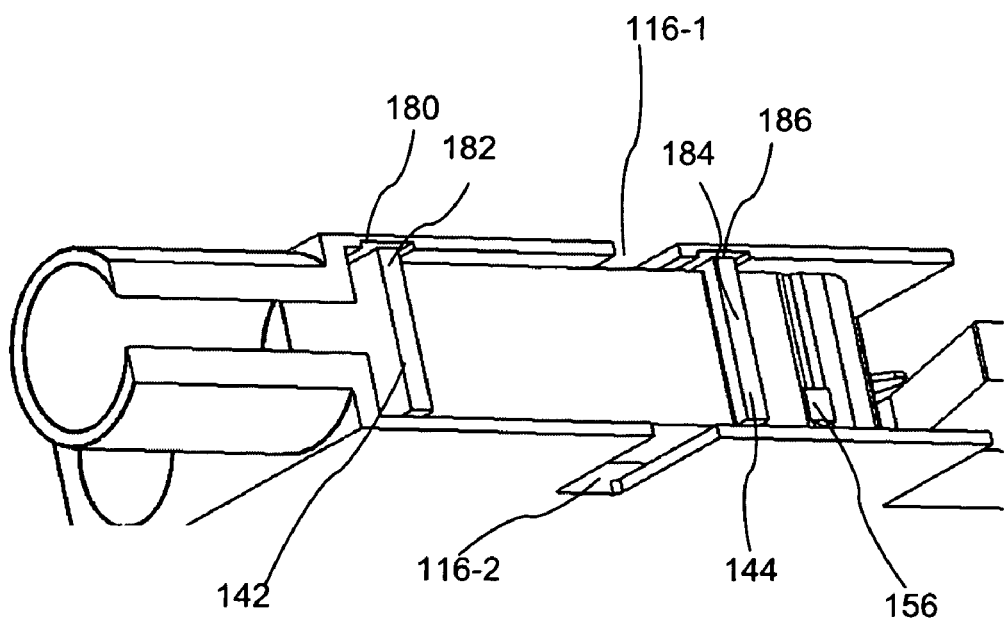

FIG. 17 provides a perspective cross-sectional view of the device of FIGS. 5A-16 with the spring and adjacent wall removed so that the side of the piston and its tabs are visible along with the edges of the proximal notch 180 and distal notch 186 in the top wall of the cylinder and proximal tab 182 and distal tab 186 on the top of the piston. As with some of the other figures, FIG. 17 also shows the top and bottom sacrificial material etching holes 116-1 and 116-2. As the proximal piston tabs (i.e. complete or partial piston rings) never reach the etching holes these holes can remain in the device as it is used. In some alternatives these etching holes may be plugged or otherwise blocked prior to putting the device to use. Techniques for sealing such openings are taught in U.S. patent application Ser. No. 10/434,103 which is referenced in the table below and is incorporated herein by reference.

Various alternatives of the present embodiment are possible. For example, instead of a single moving blade, both blades may be made movable. Instead of using a hydraulic fluid (e.g. water, a saline solution, oil, or the like), a pneumatic fluid (e.g. air, nitrogen, argon, or the like) may be use as the forcing or driving mechanism. In still other embodiments, the scissors may held in a normally closed state while the force applied by the pneumatic or hydraulic system may be used to open the scissors. In still other embodiments, the flexure (e.g. the spring as shown) may be deleted in favor of a dual acting (i.e. one that can force fluid in either direction), or single acting with use of both suction and pumping, pneumatic or hydraulic system that can be used to open and close the scissors. In some embodiments the underside of the head of the ¼ turn pin may include a compliant element to bias the pin once it is inserted and locked against shallow recess on the back side of the fixed blade. In still other embodiments, a separate inlet and outlet for the fluid may exist so that a continuous flow of fluid may be used to move the scissors between states, whereby the reversal of the fluid flow would cause a reversal in motion of the blade or blades. In still other embodiments, ramps, tabs, compliant elements, or the like may be used to force one blade against the other during movement (and particularly during a closing or cutting movement). In some embodiments the entire device may be formed from separate elements with each being fabricated using a multi-layer electrochemical fabrication process and then assembled or alternatively all elements may be fabricated in their assembled or largely assembled state. For example, the only assembly required may involve the lowering of the moveable blade into contact with the fixed blade and the insertion of the screw and or the turning of the ¼ turn pin to its locked position. In some embodiments the device may be formed from a plurality of deposited and adhered layers with layers being stacked along the Z-axis (as shown in FIG. 5A) while different layer stacking orientations may be used in other embodiments. In still further embodiments, additional etching holes may be provided (e.g. over gaps between pivot pins and surrounding structure or in other regions where narrow gaps exist). If etch holes are provided in regions where fluid or gas sealing is critical, the etch holes can be closed via bonding of structures formed along with the device itself or by attaching structures formed separately. In still further alternative embodiments the drive mechanisms of the present embodiment may be applied to other structures such as straight edged forceps, curved tip touching forceps, and any other devices that may utilize a straight hydraulic or pneumatic piston and cylinder, such as expansion devices, umbrella devices, coil delivery devices, biopsy devices, devices including ratcheting mechanisms, or the like.

Embodiment 2

Hydraulic Forceps

FIGS. 18A-25 provide various views of a second embodiment of the invention that provides hydraulic forceps. When forming the device via multi-layer, multi-material electrochemical fabrication methods it is preferred that the device be fabricated on its so as to minimize the number of layers used in forming it as well as to take advantage of the processes ability to form smooth curves in the planes of layers.

Figure 18B:
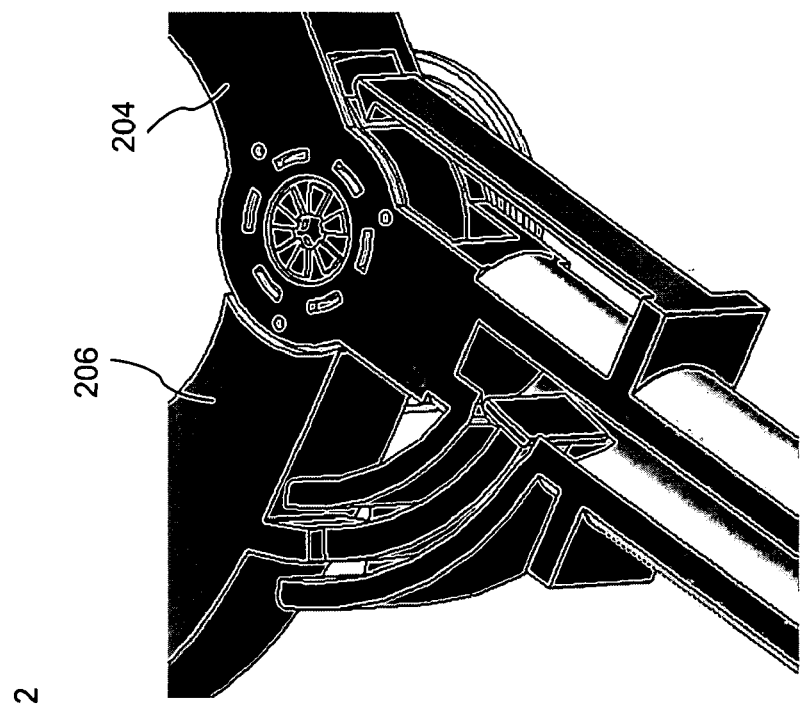
FIGS. 18A-25 provide various views of a second embodiment of the invention that provides a hydraulic forceps example.
Figure 18A:
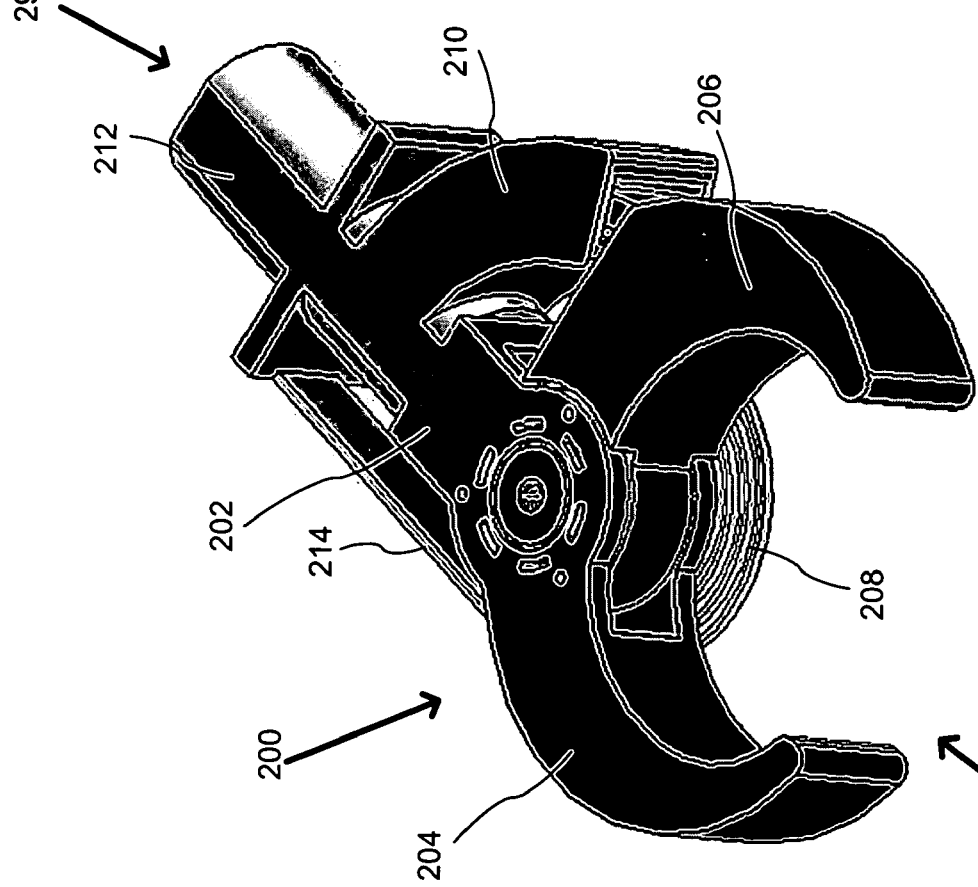
Figure 18C:
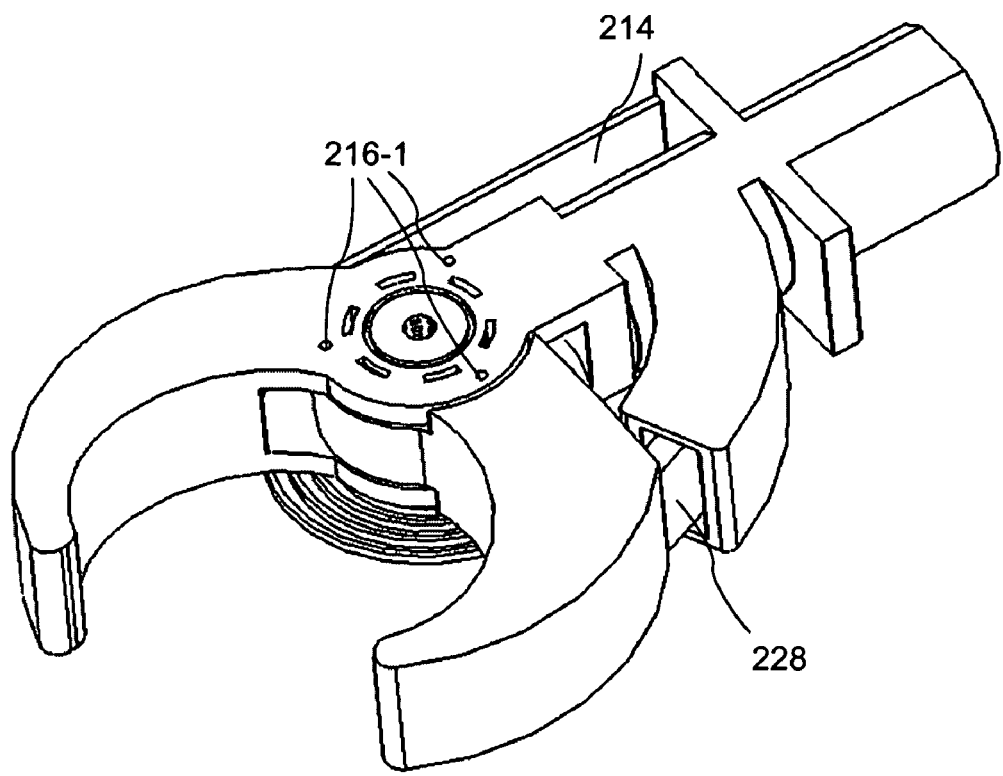
Figure 18D:
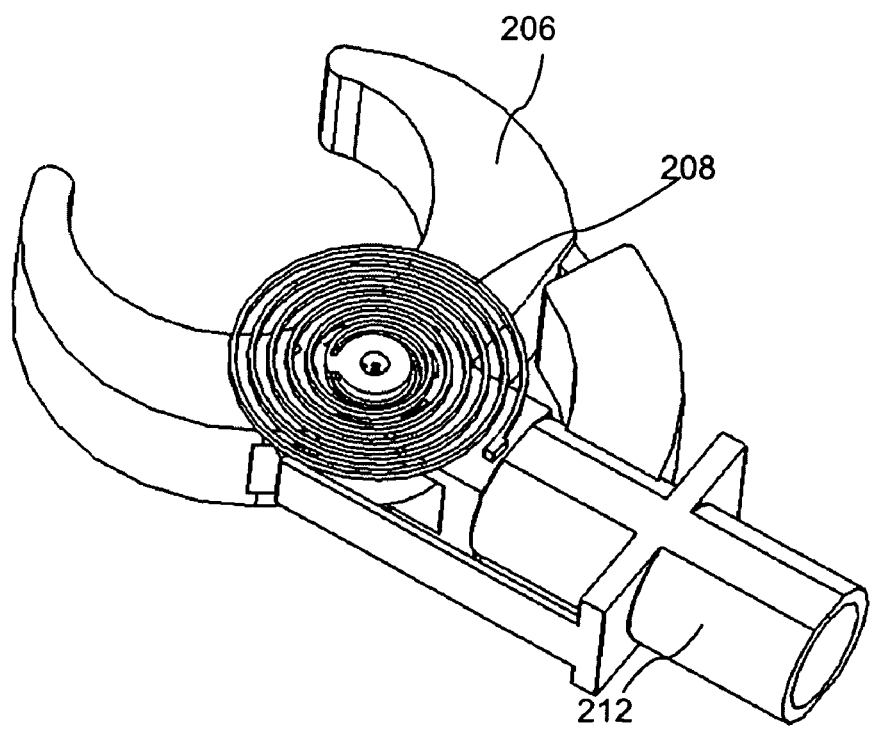

FIGS. 18A and 18B provide a perspective top view and a perspective and cut top view, respectively, of a micro-forceps device 200 according a second embodiment. FIG. 18C provides a perspective top view from another angle while FIG. 18D provide a perspective bottom view. The forceps of the present embodiment may be used directly in conjunction with a handle or they may be used at the end of a tube, wire or cable inserted into a working location via a catheter or other lumen. The forceps of the present embodiment provide curved arms/jaws 204 and 206 that provide contact at only their tips. Via the spiral spring 208 the forceps are held in a normally open state. In the present embodiment, one of the arms (arm 204) is held in a fixed position relative to the body 202 of the device while the other arm (arm 206) rotates along a curved path via the movement of a curved shaft 228 and piston head 230 located within a curved cylinder 210. The piston in the cylinder can be moved by application of a fluid pressure (e.g. a hydraulic liquid such as water, saline, oil, or the like, or a pneumatic gas such as oxygen, nitrogen, argon, or the like). In the present embodiment, three holes 216-1 and 216-2 are provided in both the top and bottom surfaces in the region of the pivot. When the jaws are positioned in a loading position a ball is dropped into each holes and then the jaws are moved to a working range which locates the balls within a notch and a surface so as to reduce vertical clearances when the forceps operate. The forceps are also supplied with a catch 214 having a proximal end that connects to the device housing 202 and a distal end the includes a catch head 220 that can inhibit the moving arm/jaw from moving from its working range back to its ball loading position.

In alternatives to the present embodiment, the jaws may take different forms, straight arms, scissor blades, plurality of tongs, jaws with fixed, pivotable, and/or compliant pads and any other configuration that may be useful in a medical application or procedure. Many of the various alternatives discussed above with regard to the first embodiment may also be used in variations of the present embodiment.

Figure 19:
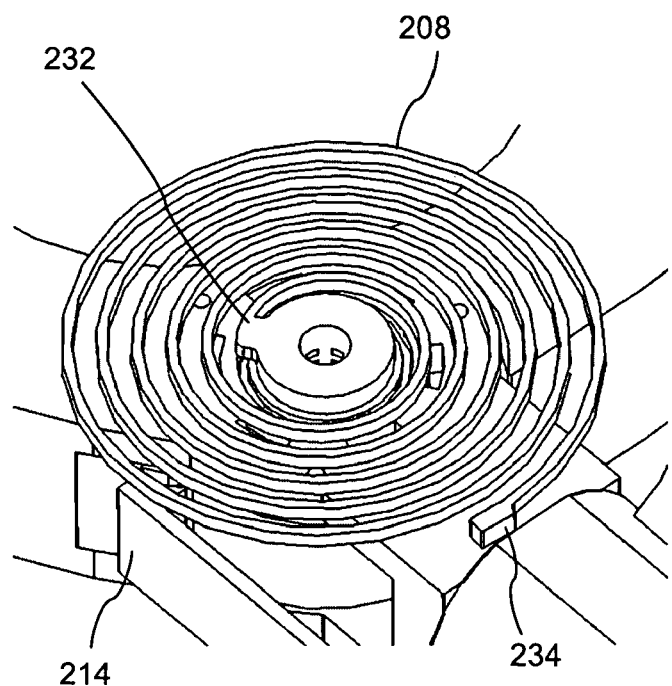

FIG. 19 provides a close up of the rotating return spring 208 and shows that one end of the spring 234 is attached to the housing while the other end is attached to an anchor 232 that rotates with the moving arm.

Figure 20:
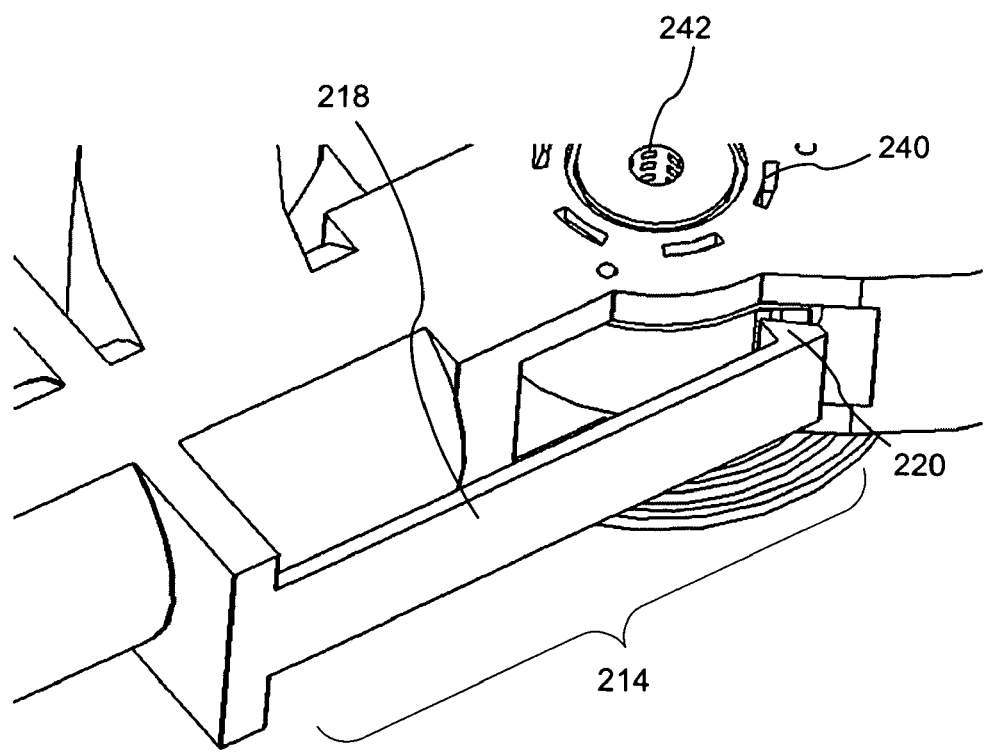

FIG. 20 provides a close up view of the catch 214, the flexure 218 and the catch head 220 prior to an initial rotation of the moveable arm to an operational position which will cause the catch head to engage a tab 238 on the rotary shaft thus inhibiting the moveable arm from moving back to the fabrication and ball loading positions without a manual release of the catch head.

Figure 21:
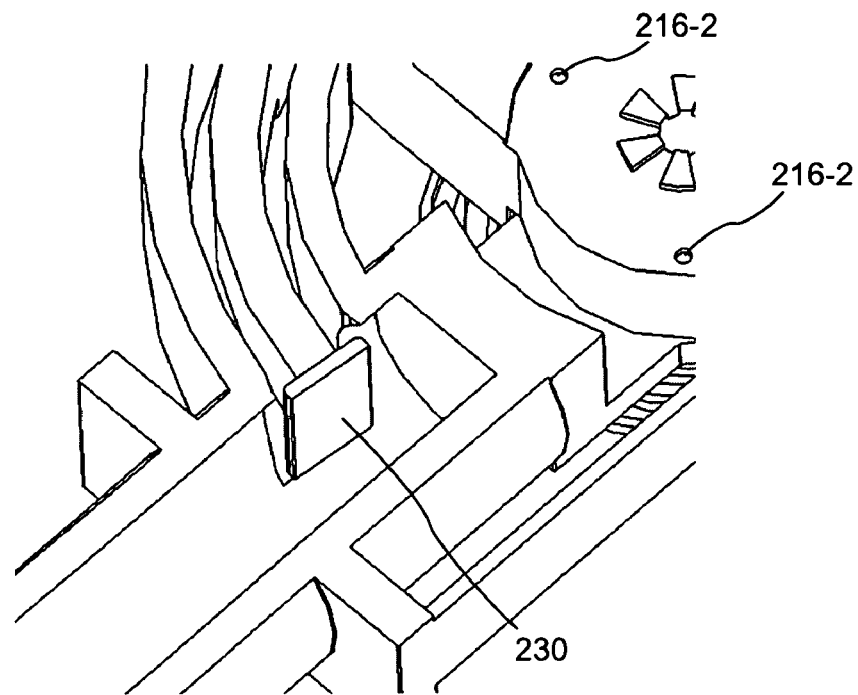

FIG. 21 provides a cross-sectional perspective view showing the fluid entrance channel 254 and the rotary piston and shaft 228 while the piston head 230 (and piston shaft and thus moveable arm) is located in its as fabricated position. In this position the piston head has sufficient space around it to allow the minimum feature size requirements to be met.

Figure 22:
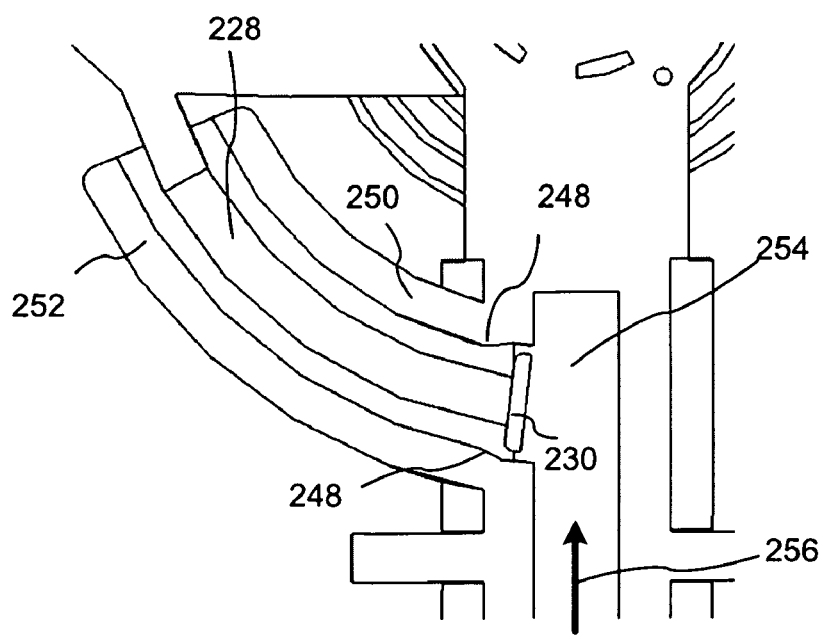

FIG. 22 provides a top cross-sectional view showing the fluid channel, piston head 230, and piston arm 228 with the piston head being moved slightly inward from its fabricated position so that the piston head as entered the initial portion of the piston channel having walls 252 where the channel begins to narrow from a larger width entrance portion to a narrowing transition portion 248. The piston and thus the moveable arm have not reached their working range yet. The working range will begin after piston has moved through the narrowing transition region 248 to the narrow region of the piston cylinder.

Figure 23:
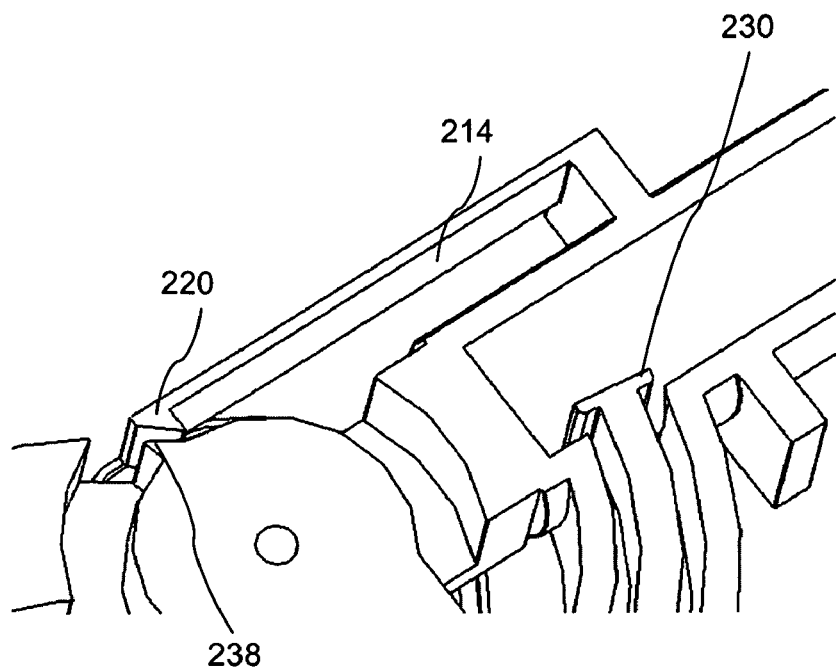

FIG. 23 provides another perspective cut view showing the piston head 230 in the fluid entry channel 254 (not in the piston cylinder) along with the catch head 220 located to the right of the tooth 238 on the moveable arm shaft 206. In other words, the device is in its fabrication state as opposed to its working state. Clockwise rotation of the arm shaft will move the piston head into the piston channel and will move the shaft tooth beyond the catch head and thus to the working range of the device.

Figure 24:
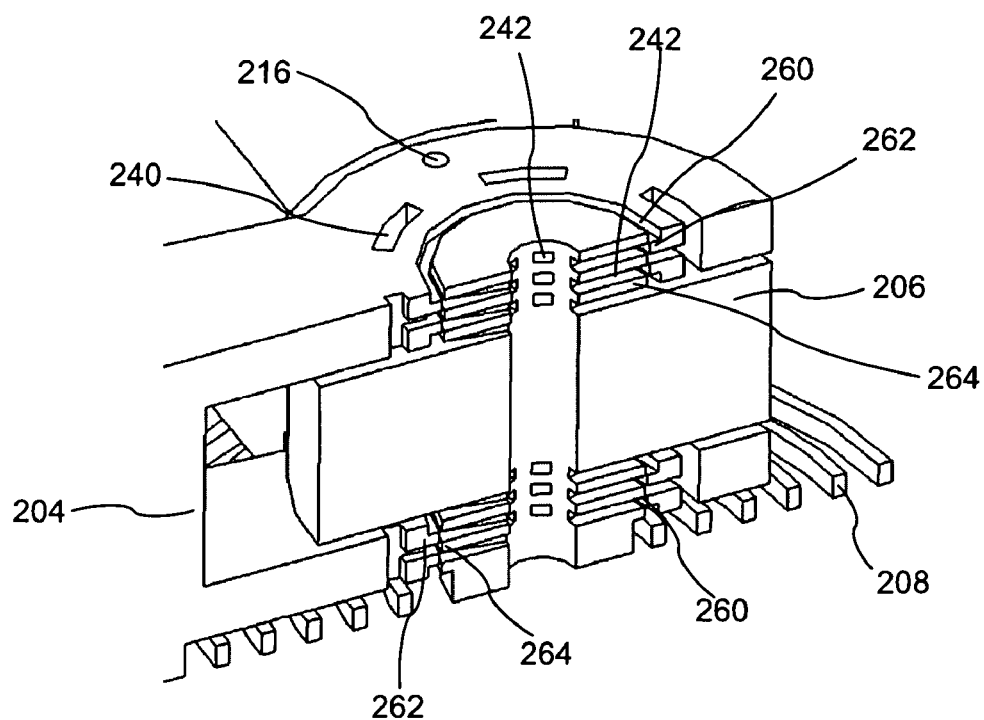

FIG. 24 depicts a perspective cross-sectional (or cut view) showing a vertical section of the device which extends through the pivot for the two arms. As can be seen, the moveable arm 206 shaft has a relatively large diameter and is hollow about its central axis. The moveable arm 206 shaft is bounded on the top and bottom by smaller diameter structures that include outward facing projections 264 and which include etching holes 242 that extend from the hollow axial opening to the regions between the outward facing projections. The proximal end of the stationary arm 204 ends in upper and lower ring like structures that bound the top and bottom of the central portion of the moveable arm shaft 206. The upper ring-like structure includes ball loading holes 216, etching holes and a plurality of inward facing projections 262. The inward and outward facing projections are formed on separate layers so that they may be formed with as small of a vertical gap as desired. As the projections have no vertical gap between them they cannot penetrate into holes in the opposing projections and taken together they form an interference bushing 260 having a spacing of any desired amount.

In some alternative embodiments, the interference bushings 260 may take on what is believed to be a more robust configuration. The inner and outer projections need not form complete rings but instead can form cylindrical and vertical patterns of alternating depressions and projections (e.g. cylindrical checker board patterns). The patterns may be selected to be repeating (such that all openings and projections achieve aligned positions multiple times per rotation) or they may be designed to be non-repeating such that in only one position per rotation all openings and projections align. Such alternative patterns may provide a greater degree of face-to-face mating and thus greater overall structural integrity during rotation and particularly during rotational motion that may be made under a significant unbalanced force. These interference bushings and alternative interference bushing techniques can apply to not only hydraulic and pneumatically driven rotary devices but also to rotary devices driven by other means. Further discussion about such cylindrical checkerboard bushings is provided below in conjunction with a discussion of FIGS. 28A-28D and 29A-29B.

Figure 25:
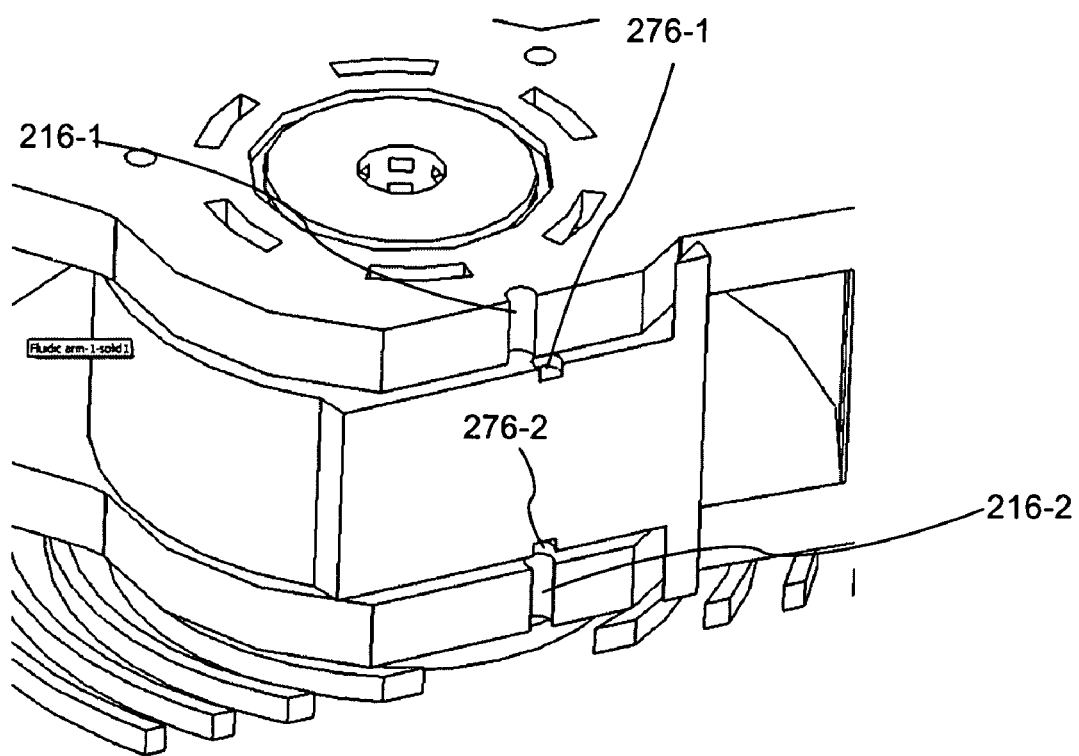

FIG. 25 provides a perspective cross-sectional (or cut view) showing a vertical section of the device which is offset toward the moveable arm as compared to the view of FIG. 24 so that recessed ball holes 216-1 and 216-2 may be seen in the upper and lower portions of the moveable arm shaft. In the present embodiment the holes on the top of the shaft and on the bottom of the shaft are not simultaneously aligned with their respective loading holes. In some embodiments the three holes on the upper surface may be located from the axis of rotation using a different radius so that the device may undergo a nearly a full 360 degree rotation before the balls realign with their loading holes. In any event, within the working range of the device, it is preferable that the balls while in their recessed holes 276-1 and 276-2 do not realign with their loading holes 216-1 and 216-2 to avoid any risk of binding or of falling out. The loading of the balls may occur on the top or bottom first (whichever is closer to the "as fabricated position) followed by a small rotation toward the working range, loading of the other balls, which in turn is followed by a rotation toward the working range that causes the catch head to extend beyond the tooth.

Embodiment 3

Hydraulic Rotary Actuator

FIGS. 26A-26B provide views of a third embodiment of the invention that provides a hydraulic rotary actuator 300 that may be used to operate a variety of useful medical tools. In the present embodiment, a saw blade 306 is attached to the shaft of the actuator. In other embodiments, other tools could be attached. Examples of such tools include drill bits, grinders, polishers, eccentric elements that convert the rotary motion into linear or nearly linear motion, eccentrics that cause oscillatory motion or vibratory motion.

The principle of operation for the rotary actuator of the present embodiment involves the use of viscous drag across a propeller to induce rotational motion. As fluid flows past the blades of the rotor, the blades pick up momentum from the flowing fluid and begin to rotate This device has two main components as seen in FIG. 26A, the "housing" 302 and "tool" 306. The housing has two ports, either of which may be used as an the inlet and outlet (as labeled 308 is the inlet while 310 is the outlet. Fluid is driven by positive pressure into inlet 308 via fluid flow in direction 322, then from the inlet 308, down the channel length in the direction of arrow 324, and around the curved channel to the outlet channel. The fluid then exits in the direction of arrow 326 through the outlet 328 in the direction of arrow 328. As shown, the housing 302 contains a number of holes used to allow etchant to enter the main channel. These holes may be sealed in a variety of ways (e.g. by use of the sealing techniques taught in U.S. patent application Ser. No. 10/434,103, reference hereafter and incorporated herein by reference. Sealing elements may be formed along with the device itself. Examples of such sealing structures and methods are taught the above noted patent application. Examples of additional techniques include sealing with tape and/or epoxy.

The tool is independent of the housing and the rotary motion. The tool may be formed along with the housing or it may be attached to the rotatable shaft subsequent to formation. Non-slipping attachment may occur, for example, via assembly based on complementary shaft configuration and/or central void configuration of a tool body. In the embodiment illustrated the tool is a saw blade. Alternatively the shaft may be formed as part of the tool and it may be inserted into a void along the axis of the rotatable actuator. Within the housing a paddlewheel element or rotor 304 has at least one portion that is located beside the flow path of the fluid and in the exemplified embodiment one half is located along the entrance path of the fluid and the other is located along the exit path thus allowing the majority of the paddlewheel's outer periphery to experience the actuation force directly.

The viscous drag from the fluid flow running down the channel forces the rotational motion of the paddlewheel. Axial and radial motion of the tool is limited by the constraints placed on the axle upon which the paddlewheel rotates. As exemplified, the cutter has a round, toothed, cutting element that is proud of the housing.

Embodiment 4

Hydraulic Rotary Actuator

Figure 27B:
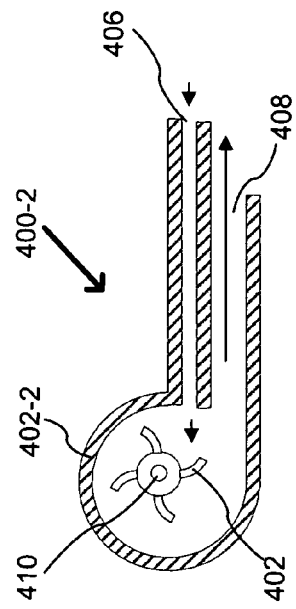
FIGS. 27A-27D provide views of four variations of a fourth embodiment of the invention that provides an impulse hydraulic rotary actuator that includes a tool in the form of a saw blade.
Figure 27D:
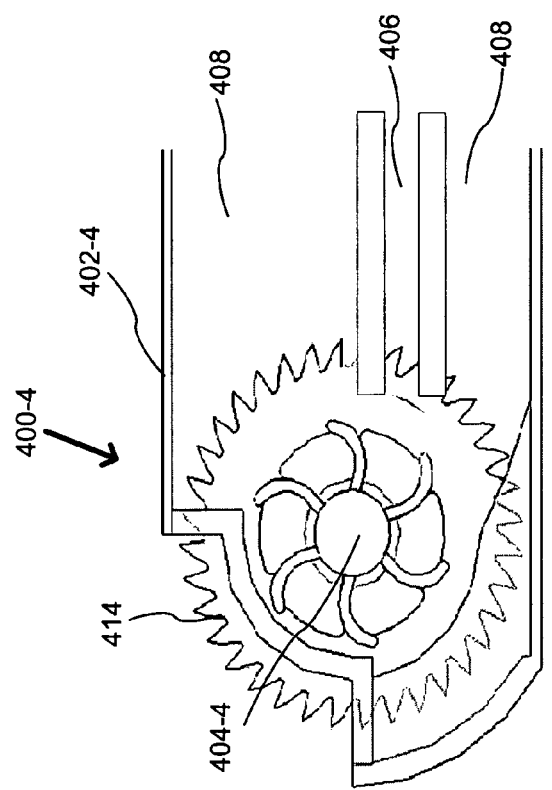
Figure 27A:
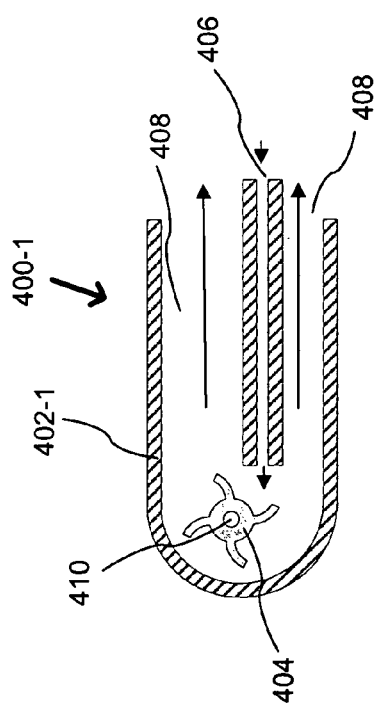

FIGS. 27A-27D provide views of four variations of a fourth embodiment of the invention that provides an impulse hydraulic rotary actuator that includes a tool in the form of a saw blade. FIG. 27A illustrates a first example of a rotary actuator includes a housing 402-1, a rotor 404 that rotates about axial 410, receives fluid from inlet 408 and dispels fluid through multiple exits 408. This device may function as a hydraulic device that uses a liquid fluid material or it may function as a pneumatic device using a gaseous fluid. The device uses the force of an incoming fluid stream from path 406 to strike paddles of rotor 404 whereby forward moment of the fluid is lost to the paddles causing rotor 404 to spin about axial 410. Fluid then flows from the device out passages 408 (e.g. via the pressure of incoming fluid forcing it out, via suction (potentially in combination with appropriate flow diverters), or via a combination, or the like. The incoming fluid is injected at high speed while the out coming fluid leaves at a much lower speed. The speed of the incoming fluid jet and its outlet position in proximity to the rotor paddles and the large flow path for exiting fluid ensures that the rotor can be made to turn. In alternate embodiments multiple inlet jets may be directed to different portion of the paddle wheel to provide more uniform force about its surface. In practice, the rotor of the present device may be functionally coupled (e.g. directly, via chain, via gears, or the like) to a tool (not shown). In some embodiments, the paddles may take on a cup or spoon-like shape and the fluid stream may be directed to an appropriate portion of the shape to cause maximum momentum transfer. In some embodiment, the rotor may include a flywheel or the like to improve smoothness of rotary motion. In still other embodiments different numbers, lengths and widths of paddles may be used. In still other embodiments, multiple rotors may operate in parallel on a single axial (e.g. the tool may be drive from between the multiple rotors) or on different axials.

Figure 27C:
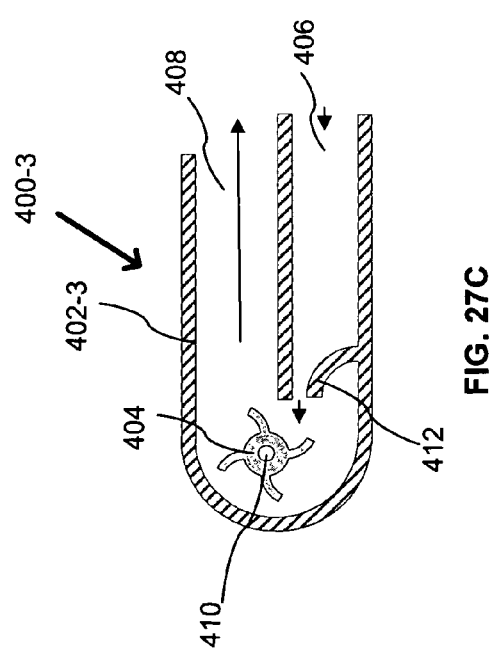

The second alternative of FIG. 27B and the third alternative of FIG. 27C are similar to that of FIG. 27A with the exception that inlet and outlet ports take on different configurations but with the intention that rotary motion is obtained by the impulse of the incoming fluid striking the paddles and transferring momentum/energy. In the drawings, like elements use like reference numbers with the exception that changes are shown by with a dash followed by the alternative number (e.g. –2 or –3). FIG. 27D shows a similar embodiment where a tool 414 (i.e. a saw blade in this example) is sandwiched between two rotors (only one is visible). After striking the paddles fluid may flow above or below the paddles to exit the device or it may flow through gaps between the paddles and sidewalls of housing 402-4.

FIGS. 27E-27F provide views of an alternative hydraulic rotary actuator, similar in appearance to that of FIG. 27D which is illustrated as including a tool in the form of rotating a saw blade located near the distal end of the device. The embodiment of FIGS. 28E and 28F contain two rotors or paddlewheels one on either side of the tool which help reduce the risk of tool or actuator damage that may result from imbalanced operation of the device.

Numerous alternates to the embodiments of FIGS. 27A-27F are possible. For example, in some alternatives the lower portion of the distal end of the device housing of FIGS. 27D and 27E could be removed such that the blade actually extends distally beyond any other elements of the device, while in still other embodiments, the blade may be retractable into the housing and extendable from the housing depending on whether it is needed at any given time. In other alternatives, any of a variety of tools may be incorporated in the device such as those mentioned elsewhere herein. In some alternatives they may be movable between working positions and non-working positions (e.g. safe positions) wherein the movement may occur via hydraulic, pneumatic, magnetic, or mechanical actuation, or the like.

Embodiment 5

Cylindrical Checkerboard Bushing

Figure 28A:
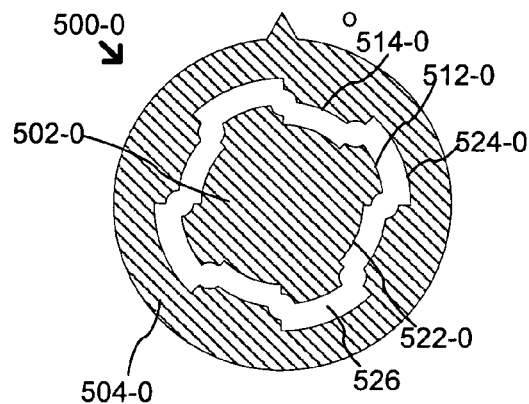
FIGS. 28A-28D provide top views of single layers of structural material defining different orientations of inner rotary structures that may be used to form a rotary checkerboard bushing according to a fifth embodiment of the invention.
Figure 28B:
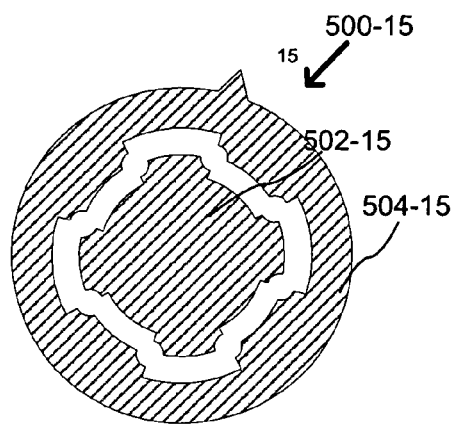
Figure 28C:
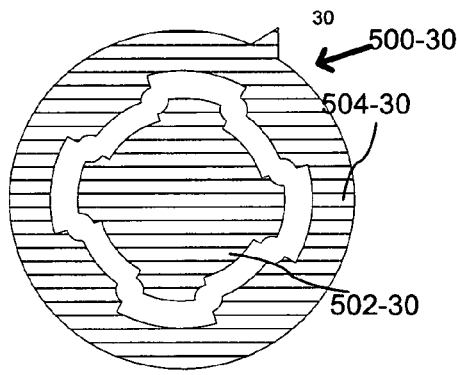
Figure 28D:
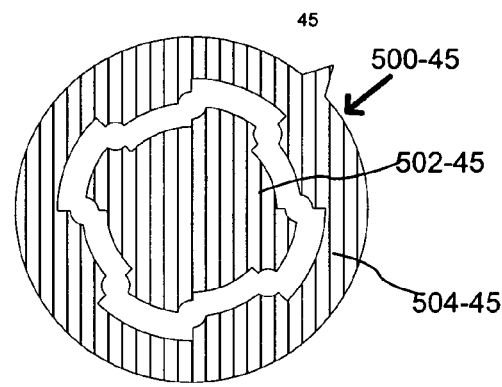
Figure 29A:
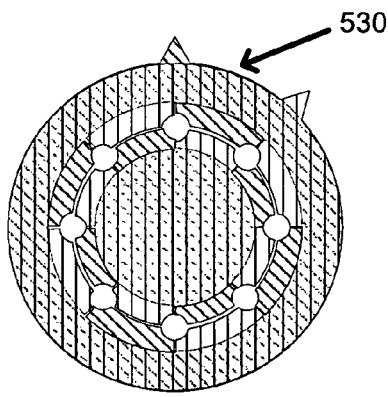
FIGS. 29A and 29B provide examples patterns of overlapping layers of an example rotary checkerboard bushing configuration according to the fifth embodiment of the invention.

FIGS. 28A-28B provide top views of single layers of structural material 500-0, 500-15, 500-30, and 500-45 defining different orientations (0°, 15°, 30°, and 45° respectively relative to the orientation of FIG. 29A) of inner rotary structures 502-0, 502-15, 502-30, and 502-5 and outer rotary structures 504-0, 504-15, 504-30, and 504-45 (each having four extensions, 512 on the outside surface of the inner structure and 514 on the inside surface of the outer structure, and retractions 522 on the outside surface of the inner structure and 524 on the inside surface of the outer structure, and having gaps 526 at least as large as a defined minimum feature size) that can be used on different layers of a structure being formed such that a cylindrical checkerboard pattern (or at least a cylindrical pattern of a substantially checkerboard configuration, i.e. cylindrical checkerboard with trimmed corners) of structural material may be created that provide smaller effective gaps for structural elements that rotate relative to one another (i.e. tighter tolerances between inner and outer rotating structures) while maintaining required minimum feature sizes so that not only are effective gaps decreased but strength of the structural interface between rotating elements is improved by allowing not only edge to edge encounter of structural material on layers (as in previously discussed interference bushing) but also resulting in enhanced face to face encounters as well. In some embodiments it may be possible to produce more complete cylindrical checker boards (i.e. no corner trimming or corner trimming that is reduced to provide effective gaps in corner regions smaller than about ½, ¼, and even ⅒ the minimum feature size for flat surface to flat surface features.

Figure 29B:
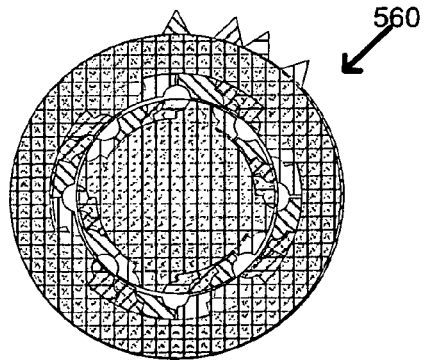

FIGS. 29A and 29B, respectively, provide top views of a two layer example and a four layer example, 530 and 560 respectively of rotational features being orientated so as to provide regions of face-to-face contact during rotational movement of the elements. In actual devices these patterns may be repeated multiple times to define a complete bearing or bushing element. In still other embodiments, instead of using the indicated numbers of protrusions and recesses per layer, fewer (e.g. 2 or 3) may be used on some layers or devices while greater numbers (5-12 or more) may be used on some layers or devices. In some embodiments single sets of rotated features may be used, multiple sets may used where sets may be repeated in the same order or in reverse order or in some mixed order. One possible advantage of embodiments using a checkerboard is that interfacing of inner and outer bushing elements is reduced to only to edge to edge interfacing when the inner and out elements are aligned to their as formed positions or to a few positions around the rotary path depending on the angular relationships between protrusions and indentations, offset orientation from layer to layer, and the like. In embodiments where formation will occur with elements in one orientation and use will be limited to incomplete circular rotary motion, it is possible that during use, edge-to-edge limited interfacing can be completely avoided. In some embodiments, etching holes or other openings may be formed on portions of the faces of the cylindrical bushing elements.

Embodiment 6 and 7

Leakage Reduction Techniques and Configurations

In some embodiments devices produced using of the multi-layer multi-material electrochemical fabrication processes discussed herein or incorporated herein by reference may provide reduced leakage of hydraulic or pneumatic fluid (e.g., water, saline, oil) that result from gaps between moving elements (e.g. pistons), and relatively fixed elements (e.g. cylinders). Reducing such leakage makes more efficient use of fluid, reduces leakages of fluid into the environment (e.g., the human body for hydraulic devices used as part of a medical device), and increases the available forces and may improve the effectiveness of applied forces.

In some embodiments, a conventional O-ring (or piston ring of relatively hard but springy material such as metal) may be added to a piston to be fabricated in order to reduce the clearance of the piston with a cylinder in which it travels. In some embodiments, the piston may be fabricated separately, the O-ring added, and the piston then inserted into the cylinder. In other embodiments, the piston may be fabricated inside the cylinder, but be displaced from its operational position to allow formation or insertion of the O-ring. One or more apertures may be provided in the cylinder to facilitate insertion of the O-ring should it be necessary. After insertion, the piston can be moved into its operating position. In some embodiments, one or more catches or other mechanical stops may be used to prevent the piston from returning to the O-ring insertion position. In some embodiments, piston rings of relatively hard, springy material may be co-fabricated along with the piston.

In some embodiments, a piston ring may be formed in-situ by extruding a suitable (e.g., elastomeric material such as a thermoplastic or thermoset polymer, although hard materials may also be used) material in liquid form into the device and hardening it. Hardening may be achieved by cooling, evaporation, chemical reaction, heat, or other methods.

Figure 30A:
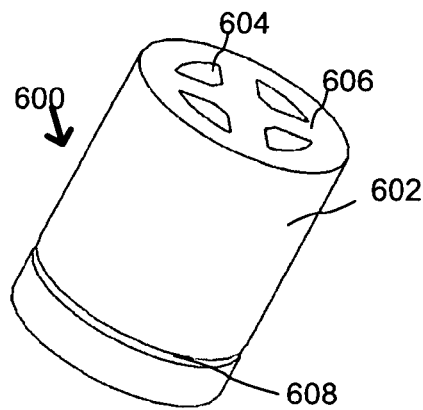
FIGS. 30A-30E various views of a piston and method for forming piston rings to provide less leakage of fluid between piston walls and cylinder walls according to a sixth embodiment of the invention.
Figure 30B:
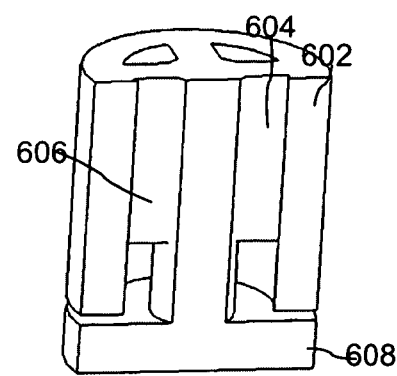
Figure 30C:
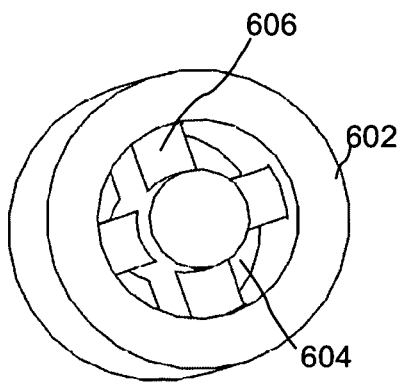
Figure 30D:
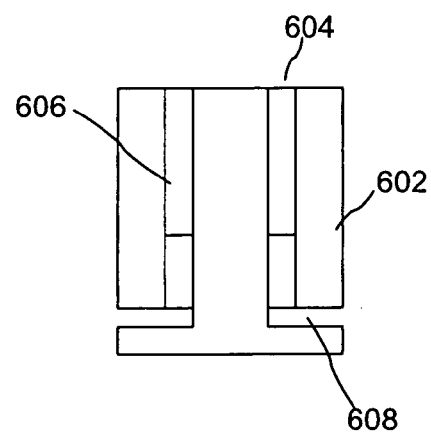
Figure 30E:
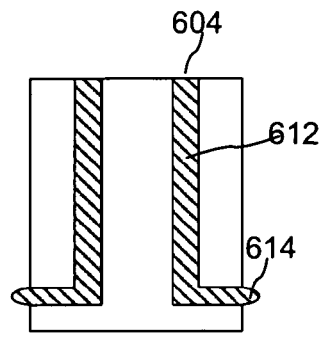

FIGS. 30A-30E illustrate a first piston ring embodiment of the invention where a solidifiable fluid is injected into one or more inlets on a piston such that a gasket or ring is extruded from a cylindrical grove that is located around a portion of the piston wall. FIGS. 30A-30C provide perspective views of a cylindrical piston 600 having at least one inlet hole 604, support ribs 606, and a groove 608 and more particularly FIGS. 30B-30C provide perspective sectional views. FIG. 30D shows a schematic cross-sectional view similar to that of FIG. 30B. When liquid 612 is injected or otherwise introduced into the inlet port 604, it extrudes out of the groove 608 as shown in FIG. 30E. If the amount of liquid introduced is well-controlled, the extent to which the liquid extrudes can also be well-controlled. The result is a piston ring 314 (or gasket) which reduces the gap between the piston and cylinder.

In some embodiments, the piston ring is formed while the piston is separate from the cylinder or in a temporary position in which there is adequate space around the groove for the liquid to extrude into the air (or another liquid) without impinging on the cylinder. In such variations, a piston ring is produced with smooth surfaces and well-defined geometry by virtue of the surface tension and viscosity of the liquid, and the piston is inserted into the cylinder or moved into its operating position such that the piston ring contacts or nearly contacts surfaces of the cylinder.

In other embodiments, the liquid may be extruded so that it contacts the cylinder (or contacts an intervening film or layer which reduces adhesion between the hardening liquid and the cylinder) such that the cylinder forms a mold for the piston ring. The path dimensions and lengths from inlet holes to groove preferably provide a uniform amount of material to all portions of the cylindrical grove so as to aid in the creation of a symmetric piston ring. In some embodiments, if the piston is rectangular in cross section instead of circular, the width of the groove may be varied locally so that the path to the corners (which are further from the center) is wider than the path to the center of each edge, to promote formation of a symmetrical piston ring. In some embodiments, multiple grooves may be used to create multiple piston rings.

In still other embodiments the piston ring maybe formed with the piston inside a temporary enclosure (e.g. formed from sacrificial material) which may be removed after formation of the ring and the piston then inserted into its cylinder (e.g. via a sloping or narrowing path).

Figure 31A:
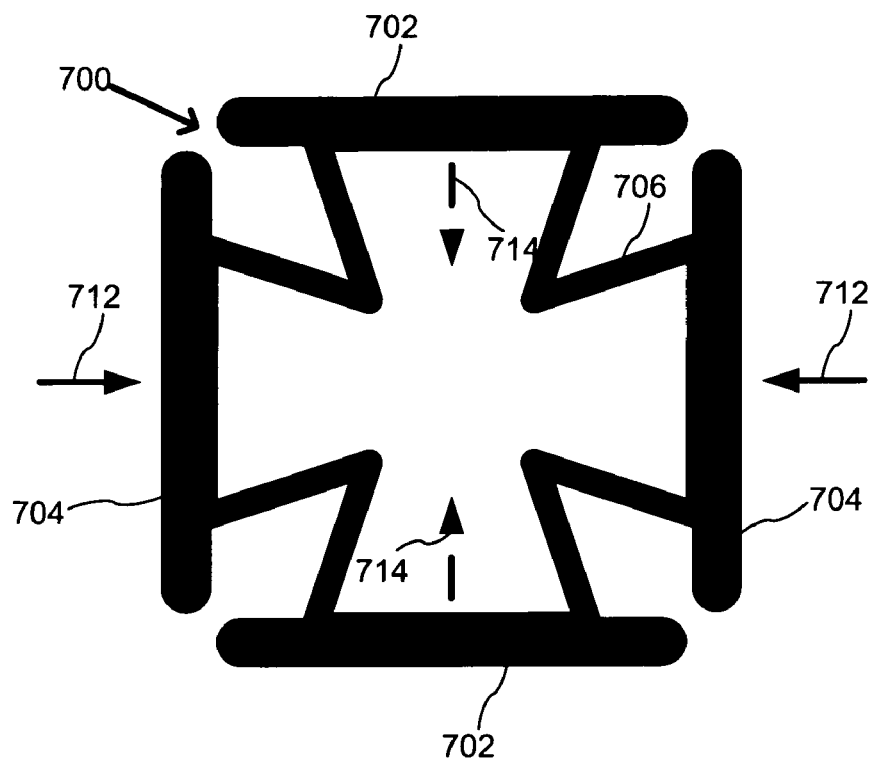
FIGS. 31A-31D various views of a piston, cylinder, and piston ring that may be used to provide less leakage of fluid between piston walls and cylinder walls according to a seventh embodiment of the invention.
Figure 31B:
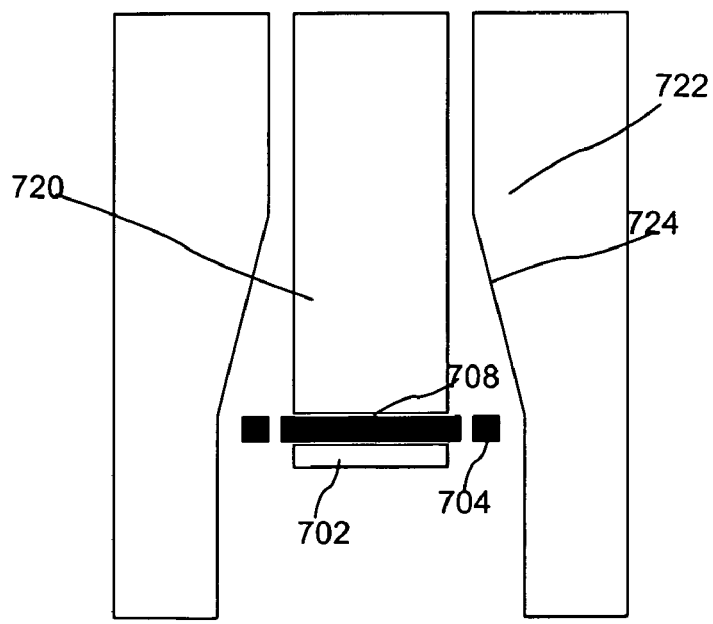
Figure 31C:
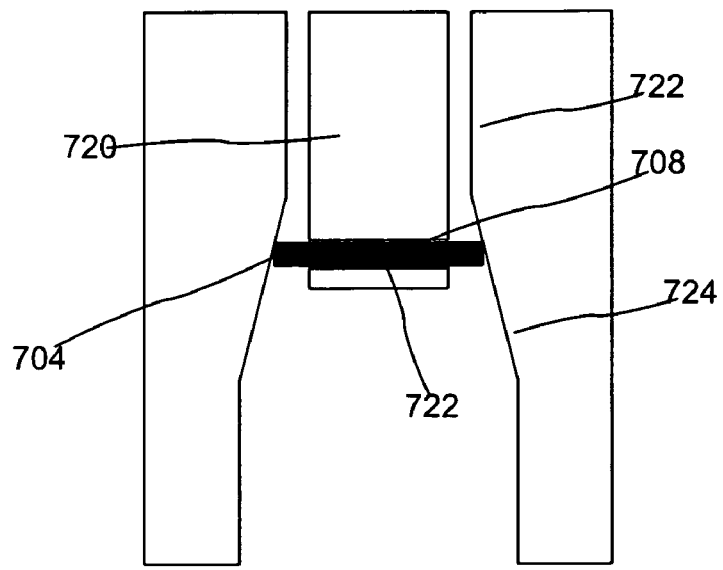
Figure 31D:
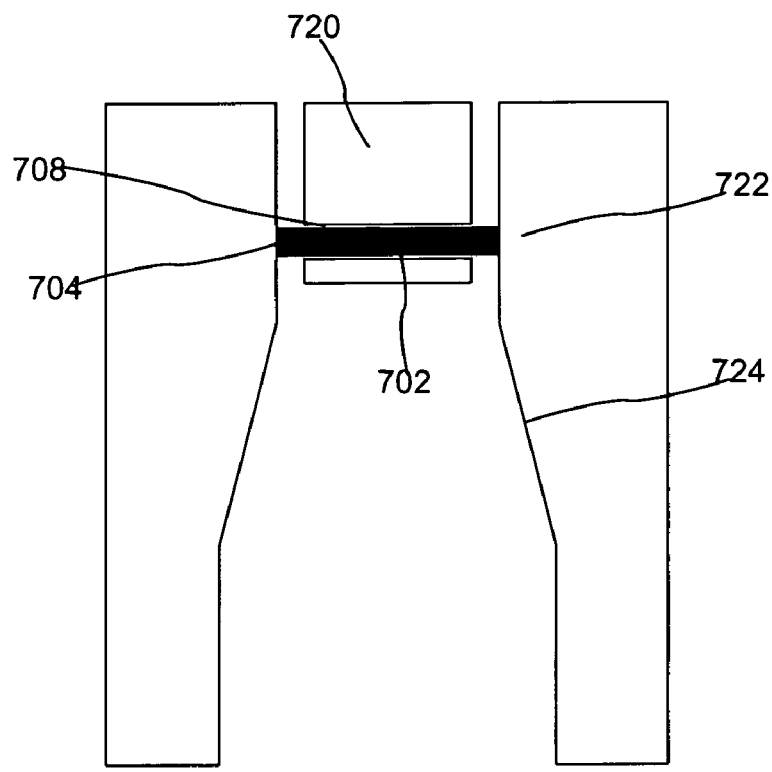

FIGS. 31A-31D provide various illustrations of a second piston ring embodiment of the invention in which a segmented region forms a closed or substantially closed ring upon compression and more particularly (in this example) via compression that primarily occurs along a single axis. In some embodiments, in particular those using a piston of rectangular cross section, a piston ring may be produced having shoes 702 and 704 and flexural elements 706 as exemplified in FIG. 31A. Such a ring may be co-fabricated along with the piston 720, occupying a groove 708 in the latter (FIG. 31B). When compressed horizontally as shown in FIG. 35, the piston ring becomes smaller in its horizontal dimension, allowing the vertical shoes 704 to fit within the cylinder and providing an improved seal against the cylinder surfaces. By virtue of the flexure design, however, the piston ring also exhibits a negative Poisson ratio-type behavior such that the ring also becomes smaller in its vertical dimensions and the horizontal shoes 702 can then also fit within the cylinder. The ability to shrink the piston ring dimensions along two axes by only compressing it along one axis is particularly valuable in devices produced using EFAB technology, since it is possible to provide smoothly-ramped surfaces within individual layers (e.g., horizontal) plane, but more difficult to do so in the plane perpendicular to that (i.e. planes like along the vertical axis or stacking axis of the layer). Thus for example, in the process of pushing the piston into the cylinder, the vertical shoes may be forced inwards by converging ramped 724 surfaces provided in or near the cylinder, thereby causing the horizontal shoes to also be forced inwards. When the piston has traveled sufficiently that all shoes have moved inwards, the piston ring can then fit within the cylinder such that the ring exerts an outwards sealing force against the cylinder walls. FIGS. 31B-31D are top views illustrating the process of inserting a piston equipped with a piston ring such as that of FIG. 31A into a cylinder 732. In FIG. 31B, the end of the piston 720 that is to hold the ring is located out of the narrow or working portion of the rectangular piston cylinder 722 so that the ring may be fabricated. In FIG. 31C, the piston 720 has been partly pushed toward the working portion of the cylinder 722 such that the vertical shoes 704 are forced inwards by interaction with the ramped surfaces 724, and the horizontal shoes 702 are forced inwards by virtue of the piston ring flexural elements. Finally, in FIG. 31D, the piston 720 has been pushed into the working region of the cylinder 722 (e.g. that portion of the cylinder in which functional operation or maximum pressure operation of the piston is to occur). Both the horizontal 702 and vertical 704 shoes have moved inwards so that they fit within the cylinder and all the shoes of the piston ring exert a sealing force against the cylinder walls.

In some embodiments, leakage between fixed and moving hydraulic elements may be reduced by use of bubbles or films of air or gas which are entrapped such that the liquid cannot easily cross the gaps between the elements. In some embodiments, the elements include features (e.g., grooves and textures) which aid in creating and maintaining these bubbles or films.

In some embodiments, expanding piston rings incorporating bellows or flexible membranes may be used to reduce leakage. These rings may be expanded temporarily or permanently by use of fluid pressure or by a phase change (e.g., solidification upon cooling) of the fluid within the rings. In the case of permanent expansion, the fluid inside the rings may be solidified (e.g., a cured epoxy) such that continuous maintenance of fluid pressure is not required.

In some embodiments, the devices described herein may be reversed such that the piston is outside the cylinder instead of inside it.

In some alternative embodiments, pistons that are to move in vertical extended cylinders (i.e. pistons and cylinders have movement axes that are parallel to the build axis may have interlayer discontinuities smoothed via one or more of the techniques set for in U.S. patent application Ser. No. 10/830,262 (which is hereby incorporated herein by reference) or via some other technique (e.g. via the spreading of a paste or other fluid by the initial movement of the piston followed by the solidification of the paste or fluid). In some embodiments having vertical moving pistons, one or more incompletely closed circular rings may be formed such that they are partially located within groves in the piston and which partially extend from the piston, Upon compression the gap or gaps in the regions may be closed or narrowed. In some embodiments where vertically moving pistons are used, gaps may be narrowed by any desired amount (particularly when piston walls and cylinder walls are smoothed) by formation of two or more layers using interference bushing or checkerboard bushing techniques. In such embodiments, and in other embodiments as well, piston and or cylinder edges may be formed of a softer material than used to form other portions of the structure such that smoothing and fitting occurs upon initial "break in" of the device (e.g. repeated movement of the piston and cylinder relative to one another either under normal operating conditions, under special conditions such as elevated temperate conditions, ramped up and down temperature conditions, high pressure or low pressure conditions and the like. In still other embodiments, piston may be formed with tapered ends (for forward and reverse motion and smooth sidewalls such that discontinuities between layers of a cylinder wall may be overcome by simply sliding past them.

In some embodiments rings may be formed such that not all portions of an existing gap are to be closed or reduced by the ring or rings but such that a sufficient portion of the gaps are closed or narrowed.

The various piston ring embodiments set forth herein may be used in various combinations with the various exemplary hydraulic devices presented herein.

FURTHER COMMENTS AND CONCLUSIONS

A number of applications were filed on Jun. 5, 2008 and Jun. 12, 2008 and each of them is incorporated herein by reference as if set forth in full. The devices of the present application can be combined with various features of the devices taught in these other applications to derive new and improved embodiments. These applications include: U.S. patent application Ser. No. 12/134,188, directed to micro umbrella devices, expansion devices and chain mail devices for use in medical applications; U.S. patent application Ser. No. 12/138,404, directed to coil delivery devices for use in medical applications; U.S. patent application Ser. No. 12/138,395, directed to biopsy devices; U.S. patent application Ser. No. 12/138,336, directed to micro-scale ratcheting devices for use in medical applications. Each of these applications is incorporated herein by reference;

In addition to the actuation methods described herein, the various elements of the various embodiments may be combined in a number of different ways to achieve similar or different results. For example the fluid flow actuation mechanisms described herein may be used in reverse such that mechanical actuation can be used to drive fluid such that the drive fluid maybe used in other devices and mechanisms. Similarly, the actuation devices can be used to provide sensing functionality instead of being used to drive other mechanical functions. In some embodiments actuation mechanism movement may occur by pulling a vacuum (e.g. extracting or pulling fluid from the actuation mechanism) as opposed pushing fluid into it.

Structural or sacrificial dielectric materials may be incorporated into embodiments of the present invention in a variety of different ways. Such materials may form a third material or higher deposited on selected layers or may form one of the first two materials deposited on some layers. Additional teachings concerning the formation of structures on dielectric substrates and/or the formation of structures that incorporate dielectric materials into the formation process and possibility into the final structures as formed are set forth in a number of patent applications filed Dec. 31, 2003. The first of these filings is U.S. Patent Application No. 60/534,184 which is entitled "Electrochemical Fabrication Methods Incorporating Dielectric Materials and/or Using Dielectric Substrates". The second of these filings is U.S. Patent Application No. 60/533,932, which is entitled "Electrochemical Fabrication Methods Using Dielectric Substrates". The third of these filings is U.S. Patent Application No. 60/534,157, which is entitled "Electrochemical Fabrication Methods Incorporating Dielectric Materials". The fourth of these filings is U.S. Patent Application No. 60/533,891, which is entitled "Methods for Electrochemically Fabricating Structures Incorporating Dielectric Sheets and/or Seed layers That Are Partially Removed Via Planarization". A fifth such filing is U.S. Patent Application No. 60/533,895, which is entitled "Electrochemical Fabrication Method for Producing Multi-layer Three-Dimensional Structures on a Porous Dielectric". Additional patent filings that provide teachings concerning incorporation of dielectrics into the EFAB process include U.S. patent application Ser. No. 11/139,262, filed May 26, 2005 by Lockard, et al., and which is entitled "Methods for Electrochemically Fabricating Structures Using Adhered Masks, Incorporating Dielectric Sheets, and/or Seed Layers that are Partially Removed Via Planarization"; and U.S. patent application Ser. No. 11/029,216, filed Jan. 3, 2005 by Cohen, et al., and which is entitled "Electrochemical Fabrication Methods Incorporating Dielectric Materials and/or Using Dielectric Substrates". These patent filings are each hereby incorporated herein by reference as if set forth in full herein.

Some embodiments may employ diffusion bonding or the like to enhance adhesion between successive layers of material. Various teachings concerning the use of diffusion bonding in electrochemical fabrication processes are set forth in U.S. patent application Ser. No. 10/841,384 which was filed May 7, 2004 by Cohen et al. which is entitled "Method of Electrochemically Fabricating Multilayer Structures Having Improved Interlayer Adhesion" and which is hereby incorporated herein by reference as if set forth in full. This application is hereby incorporated herein by reference as if set forth in full.

Some embodiments may incorporate elements taught in conjunction with other medical devices as set forth in various U.S. patent applications filed by the owner of the present application and/or may benefit from combined use with these other medical devices: Some of these alternative devices have been described in the following previously filed patent applications: (1) U.S. patent application Ser. No. 11/478,934, by Cohen et al., and entitled "Electrochemical Fabrication Processes Incorporating Non-Platable Materials and/or Metals that are Difficult to Plate On"; (2) U.S. patent application Ser. No. 11/582,049, by Cohen, and entitled "Discrete or Continuous Tissue Capture Device and Method for Making"; (3) U.S. patent application Ser. No. 11/625,807, by Cohen, and entitled "Microdevices for Tissue Approximation and Retention, Methods for Using, and Methods for Making"; (4) U.S. patent application Ser. No. 11/696,722, by Cohen, and entitled "Biopsy Devices, Methods for Using, and Methods for Making"; (5) U.S. patent application Ser. No. 11/734,273, by Cohen, and entitled "Thrombectomy Devices and Methods for Making"; (6) U.S. Patent Application No. 60/942,200, by Cohen, and entitled "Micro-Umbrella Devices for Use in Medical Applications and Methods for Making Such Devices"; and (7) U.S. patent application Ser. No. 11/444,999, by Cohen, and entitled "Microtools and Methods for Fabricating Such Tools". Each of these applications is incorporated herein by reference as if set forth in full herein.

Though the embodiments explicitly set forth herein have considered multi-material layers to be formed one after another. In some embodiments, it is possible to form structures on a layer-by-layer basis but to deviate from a strict planar layer on planar layer build up process in favor of a process that interlaces material between the layers. Such alternative build processes are disclosed in U.S. application Ser. No. 10/434,519, filed on May 7, 2003, entitled Methods of and Apparatus for Electrochemically Fabricating Structures Via Interlaced Layers or Via Selective Etching and Filling of Voids. The techniques disclosed in this referenced application may be combined with the techniques and alternatives set forth explicitly herein to derive additional alternative embodiments. In particular, the structural features are still defined on a planar-layer-by-planar-layer basis but material associated with some layers are formed along with material for other layers such that interlacing of deposited material occurs. Such interlacing may lead to reduced structural distortion during formation or improved interlayer adhesion. This patent application is herein incorporated by reference as if set forth in full.

The patent applications and patents set forth below are hereby incorporated by reference herein as if set forth in full. The teachings in these incorporated applications can be combined with the teachings of the instant application in many ways: For example, enhanced methods of producing structures may be derived from some combinations of teachings, enhanced structures may be obtainable, enhanced apparatus may be derived, and the like.

| U.S. patent application No., Filing Date U.S. application Pub No., Pub Date | Inventor, Title |
|---|---|
| 09/493,496 - Jan. 28, 2000 | Cohen, "Method For Electrochemical Fabrication" |
| 10/677,556 - Oct. 1, 2003 | Cohen, "Monolithic Structures Including Alignment and/or Retention Fixtures for Accepting Components" |
| 10/830,262 - Apr. 21, 2004 | Cohen, "Methods of Reducing Interlayer Discontinuities in Electrochemically Fabricated Three-Dimensional Structures" |
| 10/271,574 - Oct. 15, 2002 2003-0127336A - July 10, 2003 | Cohen, "Methods of and Apparatus for Making High Aspect Ratio Microelectromechanical Structures" |
| 10/697,597 - Dec. 20, 2002 | Lockard, "EFAB Methods and Apparatus Including Spray Metal or Powder Coating Processes" |
| 10/677,498 - Oct. 1, 2003 | Cohen, "Multi-cell Masks and Methods and Apparatus for Using Such Masks To Form Three-Dimensional Structures" |
| 10/724,513 - Nov. 26, 2003 | Cohen, "Non-Conformable Masks and Methods and Apparatus for Forming Three-Dimensional Structures" |
| 10/607,931- Jun. 27, 2003 | Brown, "Miniature RF and Microwave Components and Methods for Fabricating Such Components" |
| 10/841,100 - May 7, 2004 | Cohen, "Electrochemical Fabrication Methods Including Use of Surface Treatments to Reduce Overplating and/or Planarization During Formation of Multi-layer Three-Dimensional Structures" |
| 10/387,958 - Mar. 13, 2003 2003-022168A - Dec. 4, 2003 | Cohen, "Electrochemical Fabrication Method and Application for Producing Three-Dimensional Structures Having Improved Surface Finish" |
| 10/434,494 - May 7, 2003 2004-0000489A - Jan. 1, 2004 | Zhang, "Methods and Apparatus for Monitoring Deposition Quality During Conformable Contact Mask Plating Operations" |
| 10/434,289 - May 7, 2003 2004-0065555A - Apr. 8, 2004 | Zhang, "Conformable Contact Masking Methods and Apparatus Utilizing In Situ Cathodic Activation of a Substrate" |
| 10/434,294 - May 7, 2003 2004-0065550A - Apr. 8, 2004 | Zhang, "Electrochemical Fabrication Methods With Enhanced Post Deposition Processing" |
| 10/434,295 - May 7, 2003 2004-0004001A - Jan. 8, 2004 | Cohen, "Method of and Apparatus for Forming Three-Dimensional Structures Integral With Semiconductor Based Circuitry" |
| 10/434,315 - May 7, 2003 2003-0234179 A - Dec. 25, 2003 | Bang, "Methods of and Apparatus for Molding Structures Using Sacrificial Metal Patterns" |
| 10/434,103 - May 7, 2004 2004-0020782A - Feb. 5, 2004 | Cohen, "Electrochemically Fabricated Hermetically Sealed Microstructures and Methods of and Apparatus for Producing Such Structures" |
| 10/841,006 - May 7, 2004 | Thompson, "Electrochemically Fabricated Structures Having Dielectric or Active Bases and Methods of and Apparatus for Producing Such Structures" |

-continued

| U.S. patent application No., Filing Date U.S. application Pub No., Pub Date | Inventor, Title |
|---|---|
| 10/434,519 - May 7, 2003 2004-0007470A - Jan. 15, 2004 | Smalley, "Methods of and Apparatus for Electrochemically Fabricating Structures Via Interlaced Layers or Via Selective Etching and Filling of Voids" |
| 10/724,515 - Nov. 26, 2003 | Cohen, "Method for Electrochemically Forming Structures Including Non-Parallel Mating of Contact Masks and Substrates" |
| 10/841,347 - May 7, 2004 | Cohen, "Multi-step Release Method for Electrochemically Fabricated Structures" |
| 60/533,947 - Dec. 31, 2003 | Kumar, "Probe Arrays and Method for Making" |
| 60/534,183 - Dec. 31, 2003 | Cohen, "Method and Apparatus for Maintaining Parallelism of Layers and/or Achieving Desired Thicknesses of Layers During the Electrochemical Fabrication of Structures" |
| 11/733,195 - Apr. 9, 2007 | Kumar, "Methods of Forming Three-Dimensional Structures Having Reduced Stress and/or Curvature" |
| 11/506,586 - Aug. 8, 2006 | Cohen, "Mesoscale and Microscale Device Fabrication Methods Using Split Structures and Alignment Elements" |
| 10/949,744 - Sep. 24, 2004 | Lockard, "Three-Dimensional Structures Having Feature Sizes Smaller Than a Minimum Feature Size and Methods for Fabricating" |

Though various portions of this specification have been provided with headers, it is not intended that the headers be used to limit the application of teachings found in one portion of the specification from applying to other portions of the specification. For example, it should be understood that alternatives acknowledged in association with one embodiment, are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings herein with various teachings incorporated herein by reference.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

We claim:

1. A millimeter scale or microscale hydraulic or pneumatically actuated device, comprising:
   a. a device body including an inlet for receiving a fluid flow and a passage for directing the fluid flow along a desired path through the body;
   b. an actuation mechanism functionally connected to the fluid flow path which undergoes a desired mechanical movement in response to fluid flow in the passage;
   wherein the device body and actuation mechanism include a fabrication position relative to each other that provides a spacing between a first portion of the actuation mechanism relative to a first portion of the device body that is at least as large as a minimum feature size;
   wherein the device body and actuation mechanism include a working range, which is displaced from the fabrication positions, in which the first portion of the actuation mechanism moves relative to the device body during normal operation of the device, and
   wherein the first portion of the actuation mechanism is inhibited by one or more mechanical components from returning to the fabrication position during normal operation of the device.

2. The device of claim 1 additionally comprising a tool element functionally connected to the actuation mechanism for interacting with material external to the device.

3. The device of claim 2 wherein the tool element comprises a tool selected from the group consisting of: (1) a saw blade, (2) a grinder, (3) a hold and release mechanism, (4) a clamp, (5) an expander, (6) scissors, and (7) a reflector.

4. The device of claim 2 wherein the tool is used in a minimally invasive surgical procedure after traversing a tortuous path.

5. The device of claim 2 wherein the tool element includes multiple components, one or more of which is functionally connected to the device body.

6. The device of claim 1 wherein the actuation mechanism comprises a piston head and the passage is located within a piston cylinder.

7. The device of claim 6 wherein the piston cylinder is curved.

8. The device of claim 1 wherein actuation mechanism comprises an impeller that can rotate relative to the device body.

9. The device of claim 1 wherein relative movement between two elements of the device occurs at an interference bushing.

10. The device of claim 1 additionally comprising a fluid outlet that is different from the fluid inlet.

11. The device of claim 1 wherein the device is a hydraulic device.

12. The device of claim 11 wherein the device is a medical device for insertion into a body of a patient during a minimally invasive procedure wherein the device provides or aids in the providing a diagnostic evaluation of, therapeutic treatment on, or preventive treatment on the body of a patient.

13. The device of claim 1 wherein the device is a pneumatic device.

14. The device of claim 1 which is formed at least in part via a multi-layer, multi-material deposition process wherein each layer comprises at least one sacrificial material and at least one structural material and wherein each layer undergoes a planarization process and wherein the sacrificial material is removed from a plurality of layers after formation of the plurality of layers.

15. A millimeter scale or microscale hydraulic or pneumatically actuated device, comprising:
   a. a device body including an inlet for receiving a fluid flow and a passage for directing the fluid flow along a desired path through the body;
   b. an actuation mechanism functionally connected to the fluid flow path which undergoes a desired mechanical movement in response to fluid flow in the passage;
   wherein a pair of surfaces around which a first element and second element of the device move past one another during operation are separated by more than a minimum feature size on individual layers from which the device was formed,
   wherein the first and second elements are shifted relative to one another in a direction parallel to a stacking direction of the layers such that actual gaps between selected layers of the first element and selected layers of the second element are smaller than the minimum feature size, wherein the relative shifting of the first and second elements is maintained by compliant element and a retention element.

16. A millimeter scale or microscale hydraulic or pneumatically actuated device, comprising:
   a. a device body including an inlet for receiving a fluid flow and a passage for directing the fluid flow along a desired path through the body;
   b. an actuation mechanism functionally connected to the fluid flow path which undergoes a desired mechanical movement in response to fluid flow in the passage;
   wherein the device body and actuation mechanism include a fabrication position relative to each other that provides a spacing between a first portion of the actuation mechanism relative to a first portion of the device body that is at least as large as a minimum feature size;
   wherein the device body and actuation mechanism include a working range, which is displaced from the fabrication positions, in which the first portion of the actuation mechanism moves relative to the device body during normal operation of the device, and
   wherein relative movement between two elements of the device occur at a linear checkerboard bushing.

17. A millimeter scale or microscale hydraulic or pneumatically actuated device, comprising:
   a. a device body including an inlet for receiving a fluid flow and a passage for directing the fluid flow along a desired path through the body;
   b. an actuation mechanism functionally connected to the fluid flow path which undergoes a desired mechanical movement in response to fluid flow in the passage;
   wherein the device body and actuation mechanism include a fabrication position relative to each other that provides a spacing between a first portion of the actuation mechanism relative to a first portion of the device body that is at least as large as a minimum feature size;
   wherein the device body and actuation mechanism include a working range, which is displaced from the fabrication positions, in which the first portion of the actuation mechanism moves relative to the device body during normal operation of the device, and
   wherein relative movement between two elements of the device occur at a cylindrical checkerboard bushing.

* * * * *